US006996241B2

(12) United States Patent
Ray et al.

(10) Patent No.: US 6,996,241 B2
(45) **Date of Patent: *Feb. 7, 2006**

(54) TUNED FEEDFORWARD LMS FILTER WITH FEEDBACK CONTROL

(75) Inventors: Laura R. Ray, Hanover, NH (US); Alexander D. Streeter, Rochester, NY (US)

(73) Assignee: Trustees of Dartmouth College, Hanover, NH (US)

(*) Notice: Subject to any disclaimer, the term of this patent is extended or adjusted under 35 U.S.C. 154(b) by 0 days.

This patent is subject to a terminal disclaimer.

(21) Appl. No.: 10/842,714

(22) Filed: May 10, 2004

(65) Prior Publication Data

US 2004/0264706 A1 Dec. 30, 2004

Related U.S. Application Data

(63) Continuation-in-part of application No. 09/887,942, filed on Jun. 22, 2001, now Pat. No. 6,741,707.

(51) Int. Cl.
*A61F 11/06* (2006.01)

(52) U.S. Cl. ................................ 381/71.11; 381/71.12; 381/71.1; 381/71.6

(58) Field of Classification Search ............ 381/71.11, 381/71.12, 71.1, 71.6, 94.1
See application file for complete search history.

(56) References Cited

U.S. PATENT DOCUMENTS 6,396,930 B1 * 5/2002 Vaudrey et al. ............... 381/60
6,741,707 B2 * 5/2004 Ray et al. ................ 381/71.11

OTHER PUBLICATIONS

Rafaely and Jones, "Combined feedback-feedforward active noise-reducing headset—The effect of the acoustic on broadband performance," Sep. 2002, 112, pp. 981-989, *Journal of Acoustical Society of America*, Southampton, United Kingdom.

Streeter, Ray, and Collier, "Hybrid Feedforward-Feedback Active Noise Control," Thayer School of Engineering, Dartmouth College, Hanover, NH, USA.

(Continued)

*Primary Examiner*—Laura A. Grier
(74) *Attorney, Agent, or Firm*—Bourque & Assocites

(57) ABSTRACT

A method to automatically and adaptively tune a leaky, normalized least-mean-square (LNLMS) algorithm so as to maximize the stability and noise reduction performance in feedforward adaptive noise cancellation systems. The automatic tuning method provides for time-varying tuning parameters $\lambda_k$ and $\mu_k$ that are functions of the instantaneous measured acoustic noise signal, weight vector length, and measurement noise variance. The method addresses situations in which signal-to-noise ratio varies substantially due to nonstationary noise fields, affecting stability, convergence, and steady-state noise cancellation performance of LMS algorithms. The method has been embodied in the particular context of active noise cancellation in communication headsets. However, the method is generic, in that it is applicable to a wide range of systems subject to nonstationary, i.e., time-varying, noise fields, including sonar, radar, echo cancellation, and telephony. Further, the hybridization of the disclosed Lyapunov-tuned feedforward LMS filter with a feedback controller as also disclosed herein enhances stability margins, robustness, and further enhances performance.

7 Claims, 21 Drawing Sheets

OTHER PUBLICATIONS

Winberg, Johansson, Lagö, and Claesson, "A New Passive/Active Hybrid Headset for a Helicopter Application," 1999, vol. 4, No. 2, pp. 51-58, *International Journal of Acoustics and Vibration*, University of Karlskrona/Ronneby, Department of Signal Processing, Ronneby, Sweden.

Gitlin, Meadors, Jr., and Weinstein, "The Tap-Leakage Algorithm: An Algorithm for the Stable Operation of a Digitally Implemented, Fractionally Spaced Adaptive Equalizer," Oct. 1982, vol. 61, pp. 1817-1839, *The Bell System Technical Journal*, New Jersey, USA.

Mayyas and Aboulnasr, "Leaky LMS Algorithm: MSE Analysis for Gaussian Data," Apr., 1997, vol. 45, No. 4, pp. 927-934, *IEEE Transactions on Signal Processing*.

Nascimento and Sayed, "Unbiased and Stable Leakage-Based Adaptive Filters," Dec., 1999, vol. 47, No. 12, pp. 3261-3275, *IEEE Transactions on Signal Processing*.

Nascimento and Sayed, "An Unbiased and Cost-Effective Leaky-LMS Filter," 1997, 1078-1082, University of California, Los Angeles, CA, USA.

Gelfand, Wei and Krogmeier, "The Stability of Variable Step-Size LMS Algorithms," Dec., 1999, vol. 47, No. 12, pp. 3277-3288.

Ryan, Shaw, Brammer and Zhang, "Enclosure for Low-Frequency Assessment of Active Noise Reducing Circumaural Headsets and Hearing Protectors," 1993, pp. 19-20, *Canadian Acoustics*, Ottawa, Ontario, Canada.

Brammer and Pan, "Opportunities for Active Noise Control in Communication Headsets," Sep. 1998, vol. 26, No. 3, pp. 32-33, *Canadian Acoustics*, Ottawa, Ontario, Canada.

Crabtree, "Real-World Performance of Headset Active Noise Reduction Systems," ASA Special Session 3aSP: Performance of Active Noise Control Systems in Real-World Applications, Oct. 1998, pp. 1-14, Norfolk, VA, ISA.

Pan, Brammer, Goubran, Ryan and Zeral, "Broad-Band Active Noise Reduction in Communication Headsets," Mar. 1994 vol. 22, No. 3, pp. 113-114, *Canadian Acoustics*.

Cartes, Ray and Collier, "Experimental evaluation of leaky least-mean-square algorithms for active noise reduction in communication headsets," Apr. 2002, vol. 111, No. 4, pp. 1758-1771, *J. Acoustic Society of America*.

Cartes, "Lyapunov Tuning and Optimization of Feedforward Noise Reduction for Single-Point, Single-Source Cancellation," Oct. 2000, pp. 1-193, Thayer School of Engineering, Dartmouth College, Hanover, New Hampshire, USA.

Ward, "Effects of High-Intensity Sound", 1997, pp. 1497-1507.

* cited by examiner (a)SNR=2

$V_{k+1} - V_k$ : CANDIDATE 1

$V_{k+1} - V_k$ : CANDIDATE 2

$V_{k+1} - V_k$ : CANDIDATE 3

(b)SNR=10

$V_{k+1} - V_k$ : CANDIDATE 1

$V_{k+1} - V_k$ : CANDIDATE 2

$V_{k+1} - V_k$ : CANDIDATE 3

(c)SNR=100

| TUNING LAW | SIGNAL-NOISE RATIO | | |
|---|---|---|---|
| | 2 | 10 | 100 |
| CANDIDATE 1: | | | |
| $MIN(V_{k+1} - V_k)$ | -0.4511 | -0.4447 | -0.4442 |
| $MAX(V_{k+1} - V_k)$ | 0.2690 | 0.2668 | 0.2667 |
| $\mu_k$ | 3.0759e+05 | 2.2879e+04 | 2.7138e+02 |
| $\lambda_k$ | 0.9969 | 0.9998 | 1.000 |
| CANDIDATE 2: | | | |
| $MIN(V_{k+1} - V_k)$ | -0.9988 | -1.0000 | -1.0000 |
| $MAX(V_{k+1} - V_k)$ | 0.9148 | 0.9932 | 0.9999 |
| $\mu_k$ | 8.7449e+05 | 6.8354e+04 | 8.1410e+02 |
| $\lambda_k$ | 0.9912 | 0.9931 | 0.9999 |
| CANDIDATE 3: | | | |
| $MIN(V_{k+1} - V_k)$ | -0.9999 | -0.9996 | -1.0000 |
| $MAX(V_{k+1} - V_k)$ | 0.5197 | 0.3451 | 0.3326 |
| $\mu_k$ | 2.9051e+05 | 3.3373e+04 | 4.0694e+02 |
| $\lambda_k$ | 0.6296 | 0.9725 | 0.9997 |

FIG. 7

| ALGORITHM AND SPL | MEAN LEAKAGE FACTOR | STANDARD DEVIATION OF LEAKAGE FACTOR (X 10000) |
|---|---|---|
| LNLMS(80) 80dB<br>LNLMS(100) 100dB | 0.9999306<br>0.999988305 | 0 (CONSTANT)<br>0 (CONSTANT) |
| CANDIDATE 1 80dB<br>100dB | 0.999639928<br>0.999996425 | 0.5965676<br>0.0061112 |
| CANDIDATE 2 80dB<br>100dB | 0.999999698<br>0.999999997 | 0.0004974<br>0.0000035 |
| CANDIDATE 3 80dB<br>100dB | 0.999999356<br>0.999999996 | 0.0008408<br>0.0000065 |

FIG. 9

TUNED FEEDFORWARD LMS FILTER WITH FEEDBACK CONTROL

STATEMENT OF RELATED APPLICATION

This application is a continuation-in-part of U.S. patent application Ser. No. 09/887,942 filed Jun. 22, 2001 now U.S. Pat. No. 6,741,707 and incorporated herein by reference Force. The Government has certain rights in this invention.

STATEMENT OF GOVERNMENT INTEREST

The invention was made with the Government support under Grant No. F41624-99-C-606 awarded by the United States Air Force. The Government has certain rights in this invention.

FIELD OF THE INVENTION

The present invention relates to a method for automatically and adaptively tuning a leaky, normalized least-mean-square (LMS) algorithm so as to maximize the stability and noise reduction performance of feedforward adaptive noise cancellation systems and to eliminate the need for ad-hoc, empirical tuning and more specifically, to the hybridization of a Lyapunov-tuned feedforward LMS filter with a feedback controller so as to enhance stability margins, robustness, and further enhance performance.

BACKGROUND OF THE INVENTION

Noise cancellation systems are used in various applications ranging from telephony to acoustic noise cancellation in communication headsets. There are, however, significant difficulties in implementing such stable, high performance noise cancellation systems.

In the majority of adaptive systems, the well-known LMS algorithm is used to perform the noise cancellation. This algorithm, however, lacks stability in the presence of inadequate excitation, non-stationary noise fields, low signal-to-noise ratio, or finite precision effects due to numerical computations. This has resulted in many variations to the standard LMS algorithm, none of which provide satisfactory performance over a range of noise parameters.

Among the variations, the leaky LMS algorithm has received significant attention. The leaky LMS algorithm, first proposed by Gitlin et al. introduces a fixed leakage parameter that improves stability and robustness. However, the leakage parameter improves stability at a significant expense to noise reduction performance.

Thus, the current state-of-the-art LMS algorithms must tradeoff stability and performance through manual selection of tuning parameters, such as the leakage parameter. In such noise cancellation systems, a constant, manually selected tuning parameter cannot provide optimized stability and performance for a wide range of different types of noise sources such as deterministic, tonal noise, stationary random noise, and highly nonstationary noise with impulsive content, nor adapt to highly variable and large differences in the dynamic ranges evident in real-world noise environments. Hence, "worst case", i.e., highly variable, nonstationary noise environment scenarios must be used to select tuning parameters, resulting in substantial degradation of noise reduction performance over a full range of noise fields.

Presently, commercial active noise reduction (ANR) technology uses feedback control to reduce unwanted sound. A feedback topology is shown in FIG. 16. Here, the measured error signal $e_k$ is minimized through an infinite impulse response feedback compensator designed using traditional frequency-domain methods. The feedback controller seeks to force the phase between the output signal and the error signal equal to −180 degrees for as much as the ANR frequency band as possible. In active noise control, a high-gain control law is required to achieve this objective and to maximum ANR performance. However, a high-gain control law leaves inadequate stability margins, and such systems destabilize easily in practice, as the transfer function of the system can vary substantially with environmental conditions. In order to provide adequate stability margins, ANR performance is sacrificed, thus present feedback technology exhibits narrowband performance and "spillover" or creation of noise outside of the ANR band. Present commercial technology implements feedback control using analog circuitry.

SUMMARY OF THE INVENTION

The present invention discloses a method to automatically and adaptively tune a leaky, normalized least-mean-square (LNLMS) algorithm so as to maximize the stability and noise reduction performance in feedforward adaptive noise cancellation systems. The automatic tuning method provides for time-varying tuning parameters $\lambda_k$ and $\mu_k$ that are functions of the instantaneous measured acoustic noise signal, weight vector length, and measurement noise variance. The method addresses situations in which signal-to-noise ratio varies substantially due to nonstationary noise fields, affecting stability, convergence, and steady-state noise cancellation performance of LMS algorithms. The method has been embodied in the particular context of active noise cancellation in communication headsets. However, the method is generic, in that it is applicable to a wide range of systems subject to nonstationary, i.e., time-varying, noise fields, including sonar, radar, echo cancellation, and telephony. Further, the hybridization of the disclosed Lyapunov-tuned feedforward LMS filter with a feedback controller as also disclosed herein enhances stability margins, robustness, and further enhances performance.

It is important to note that the present invention is not intended to be limited to a device or method which must satisfy one or more of any stated or implied objects or features of the invention. It is also important to note that the present invention is not limited to the preferred, exemplary, or primary embodiment(s) described herein. Modifications and substitutions by one of ordinary skill in the art are considered to be within the scope of the present invention, which is not to be limited except by the following claims.

BRIEF DESCRIPTION OF THE DRAWINGS

These and other features and advantages of the present invention will be better understood by reading the following detailed description, taken together with the drawings wherein.

Figure 5:
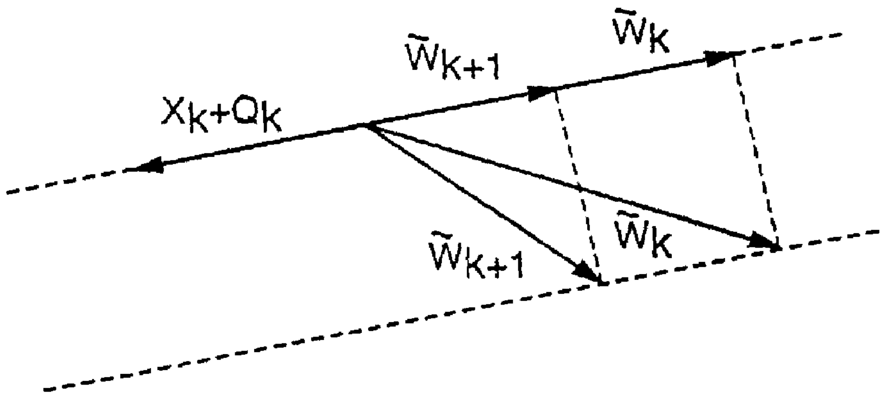
Figure 8:
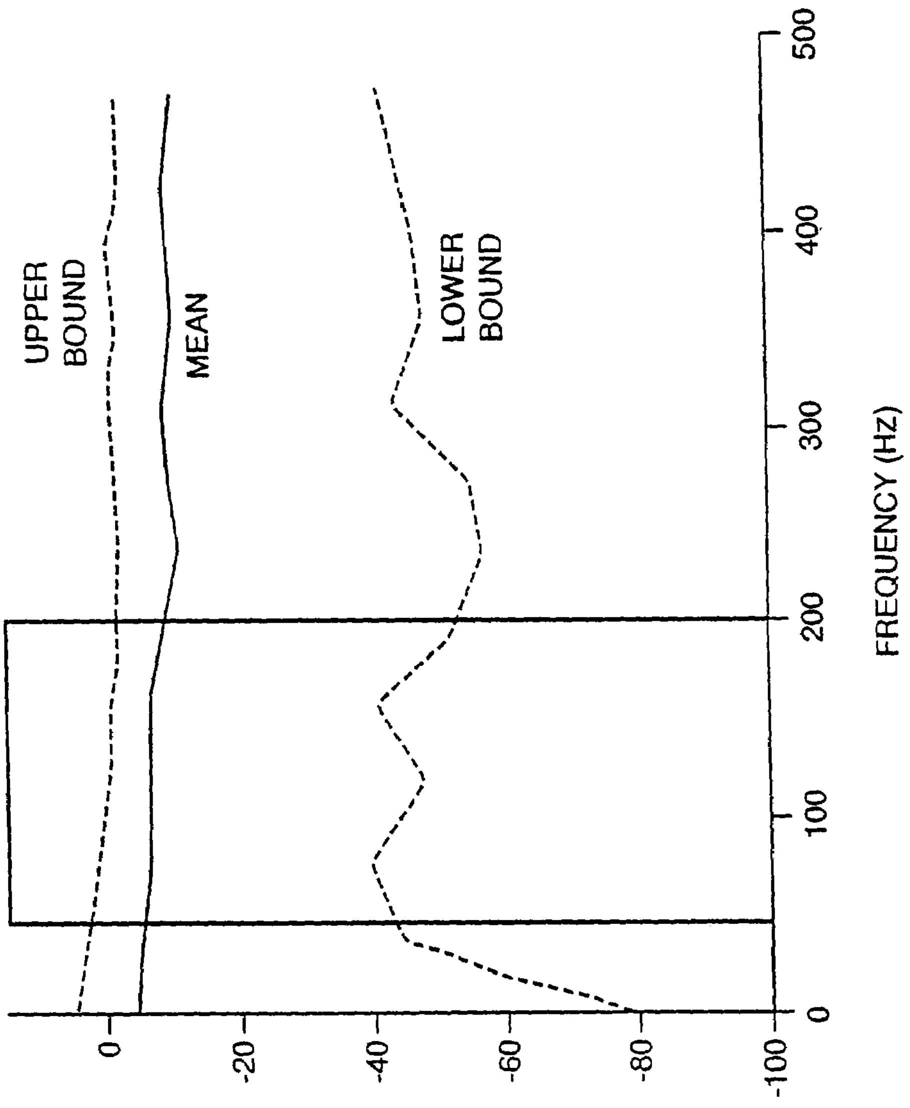
Figure 10:
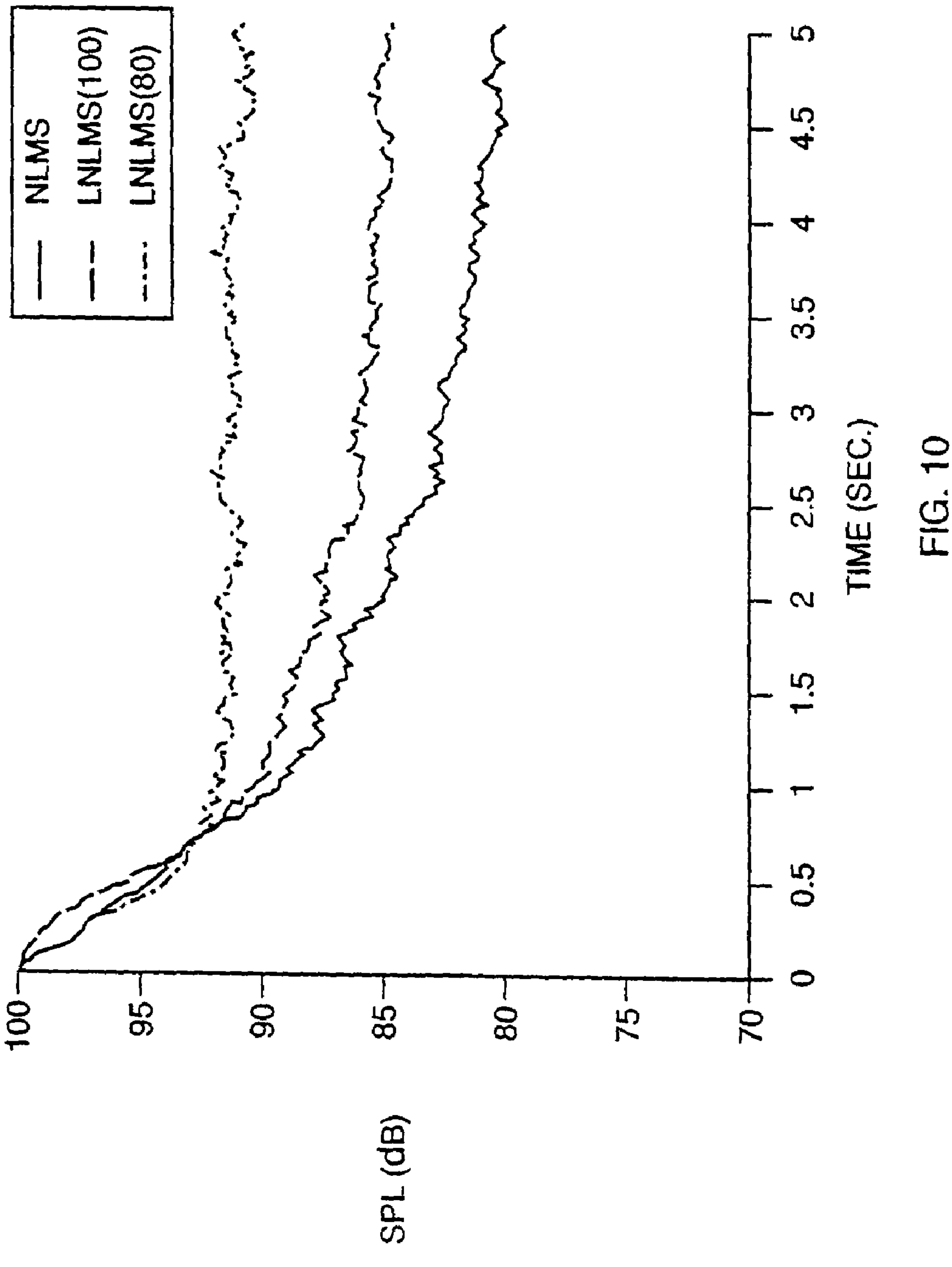
Figure 11:
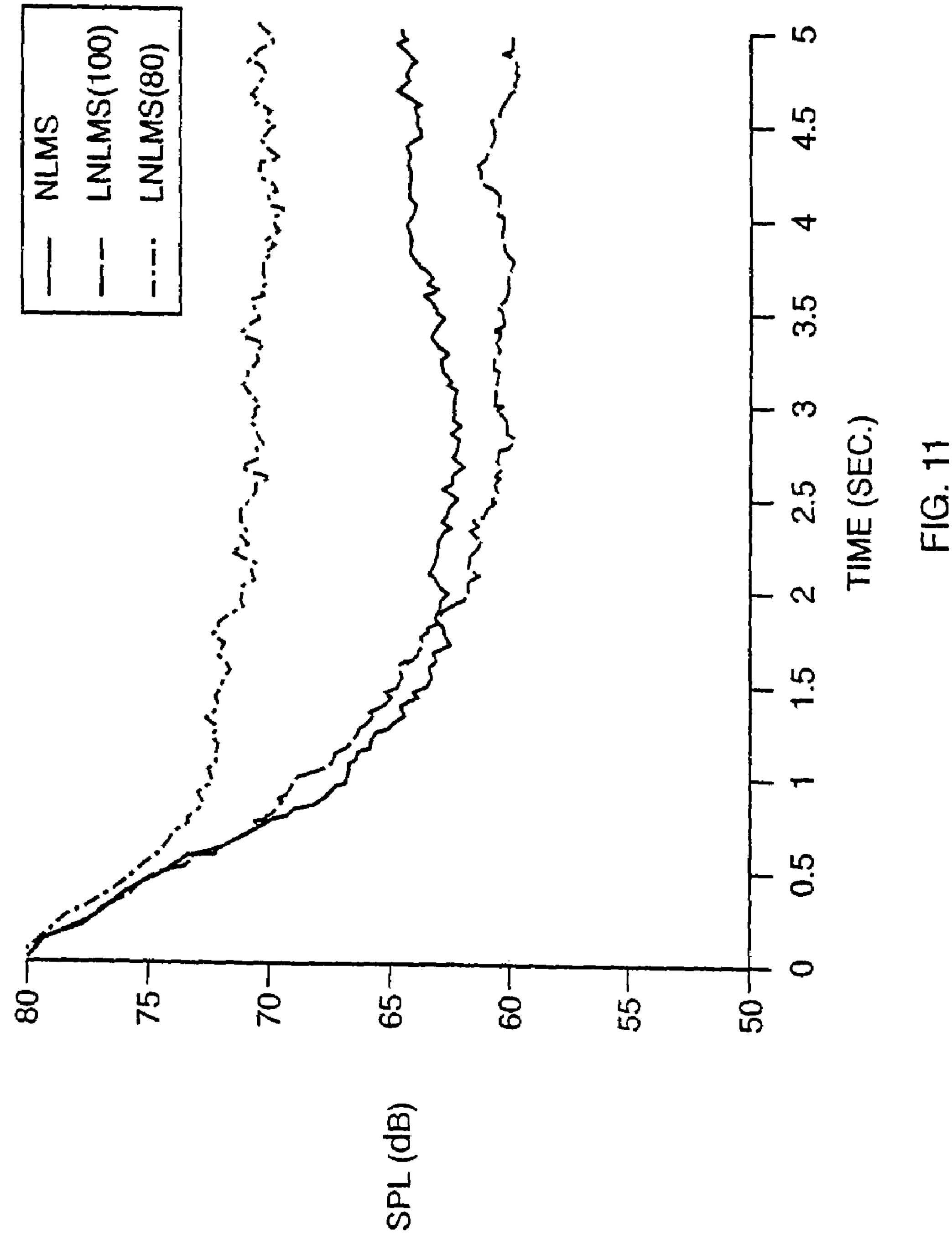
Figure 12A:
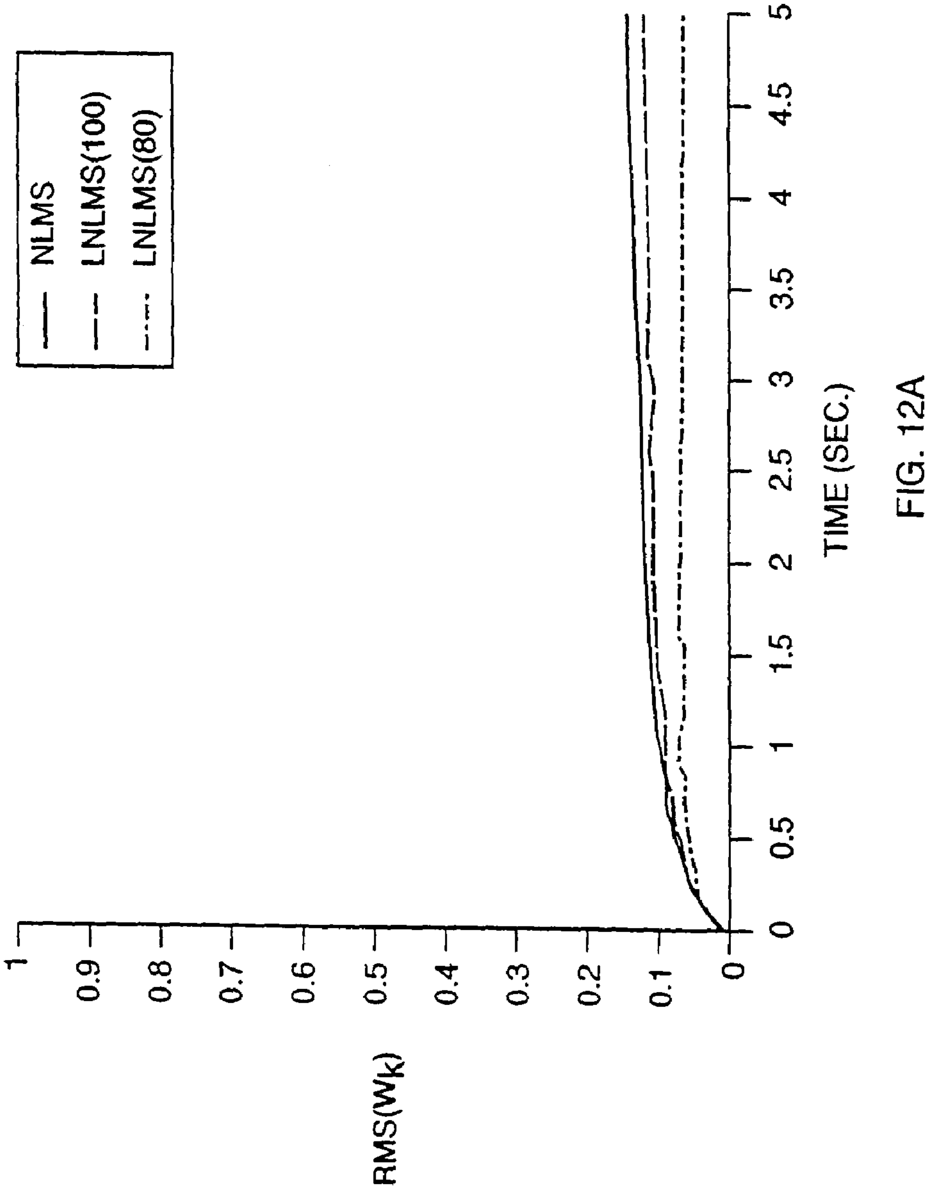
Figure 12B:
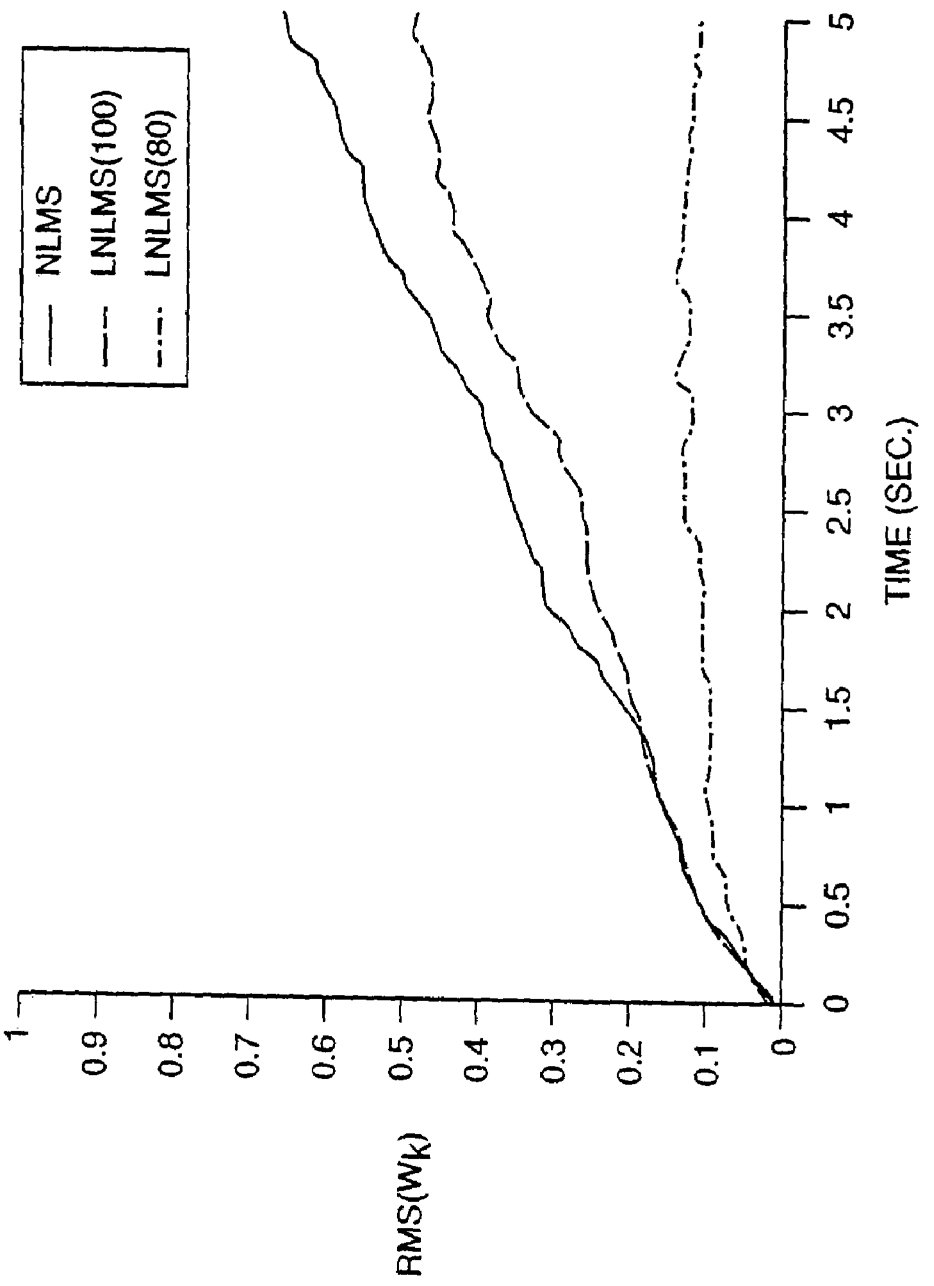
Figure 13:
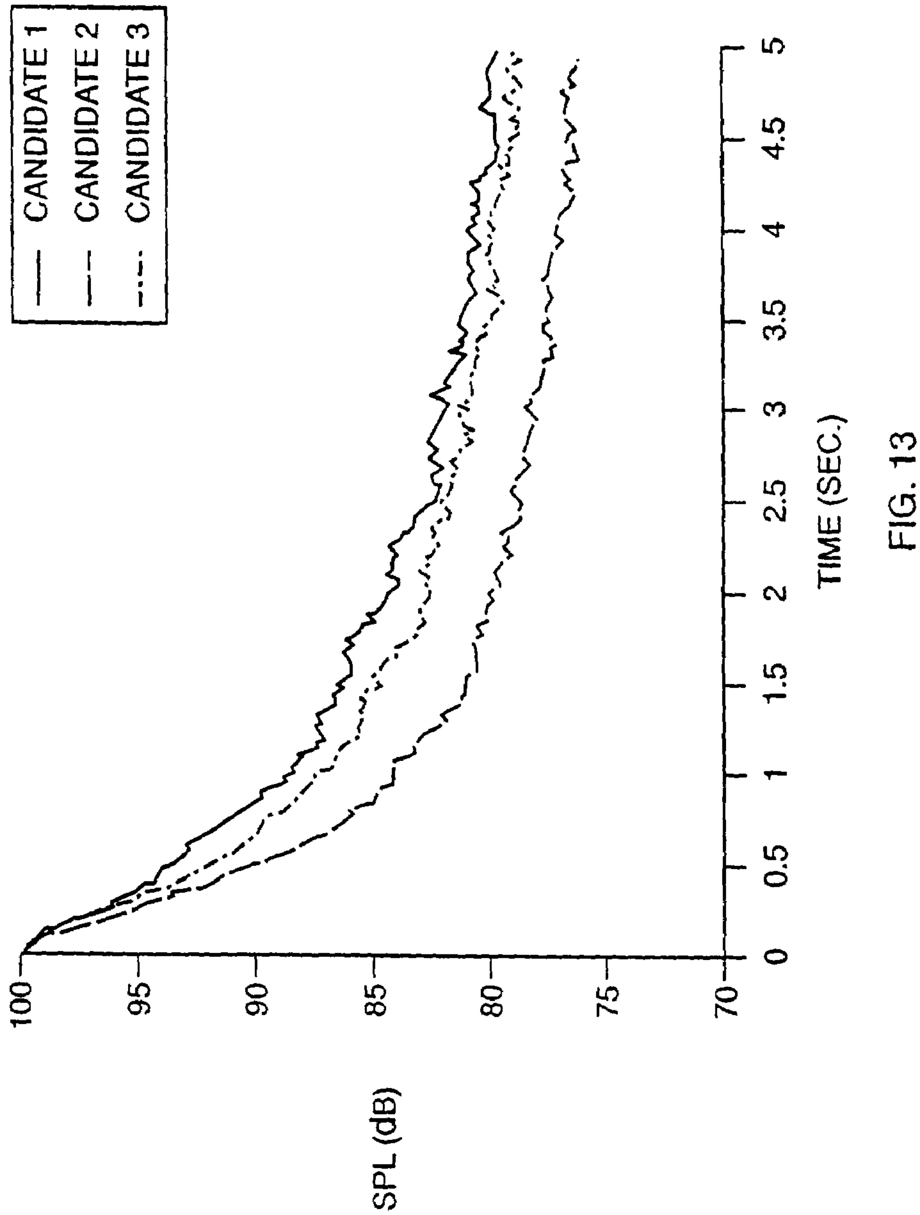
Figure 14:
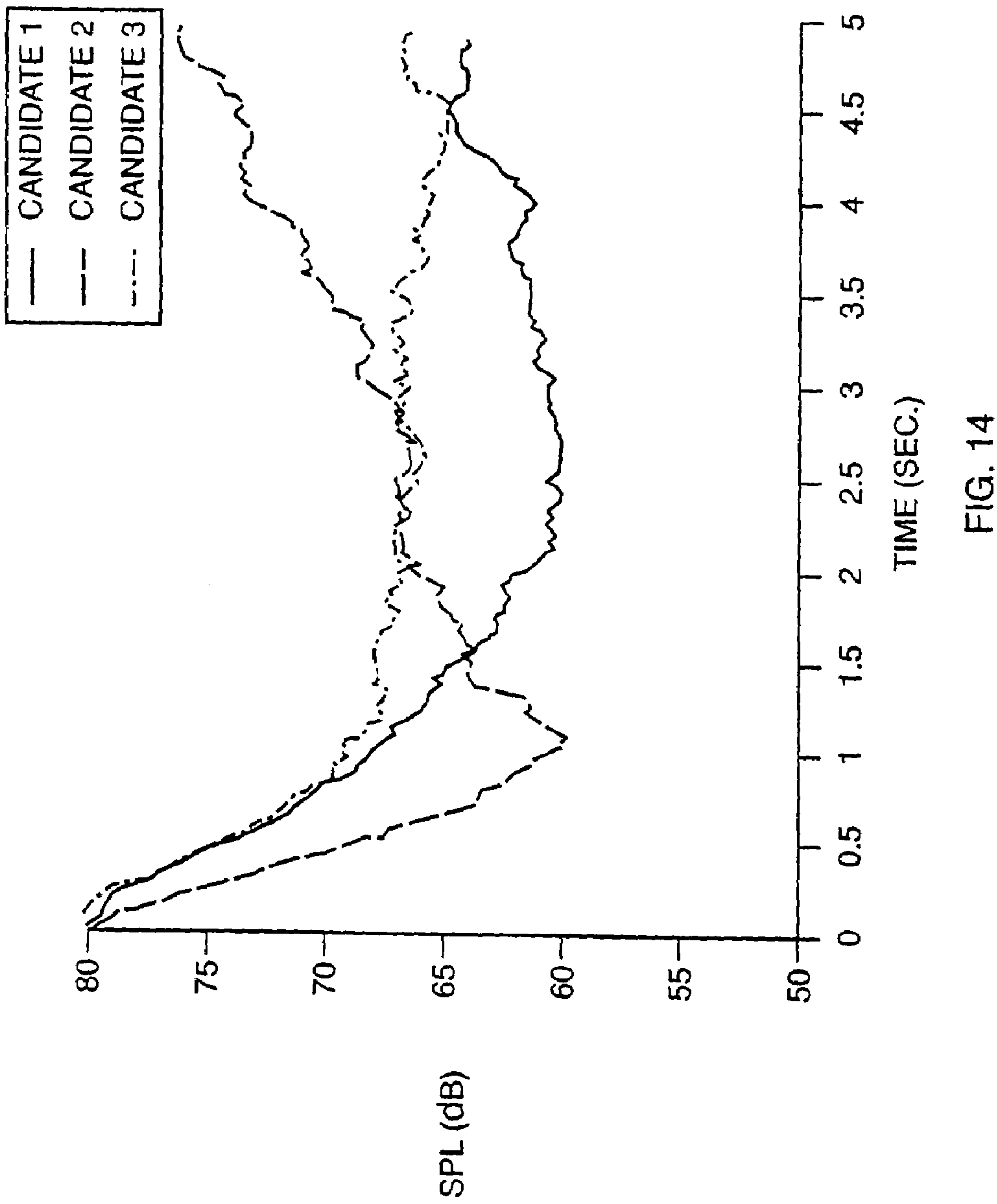
Figure 15A:
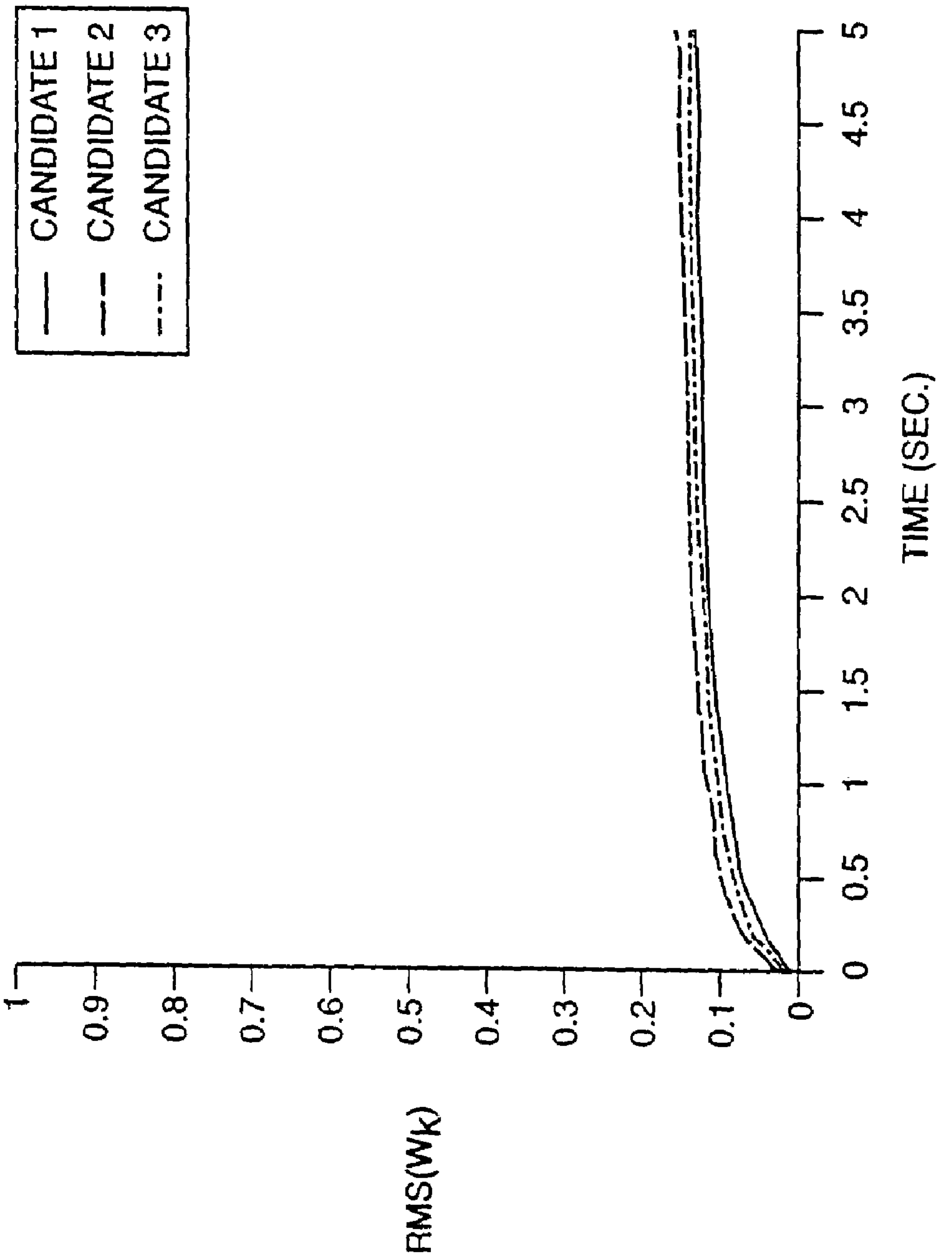
Figure 15B:
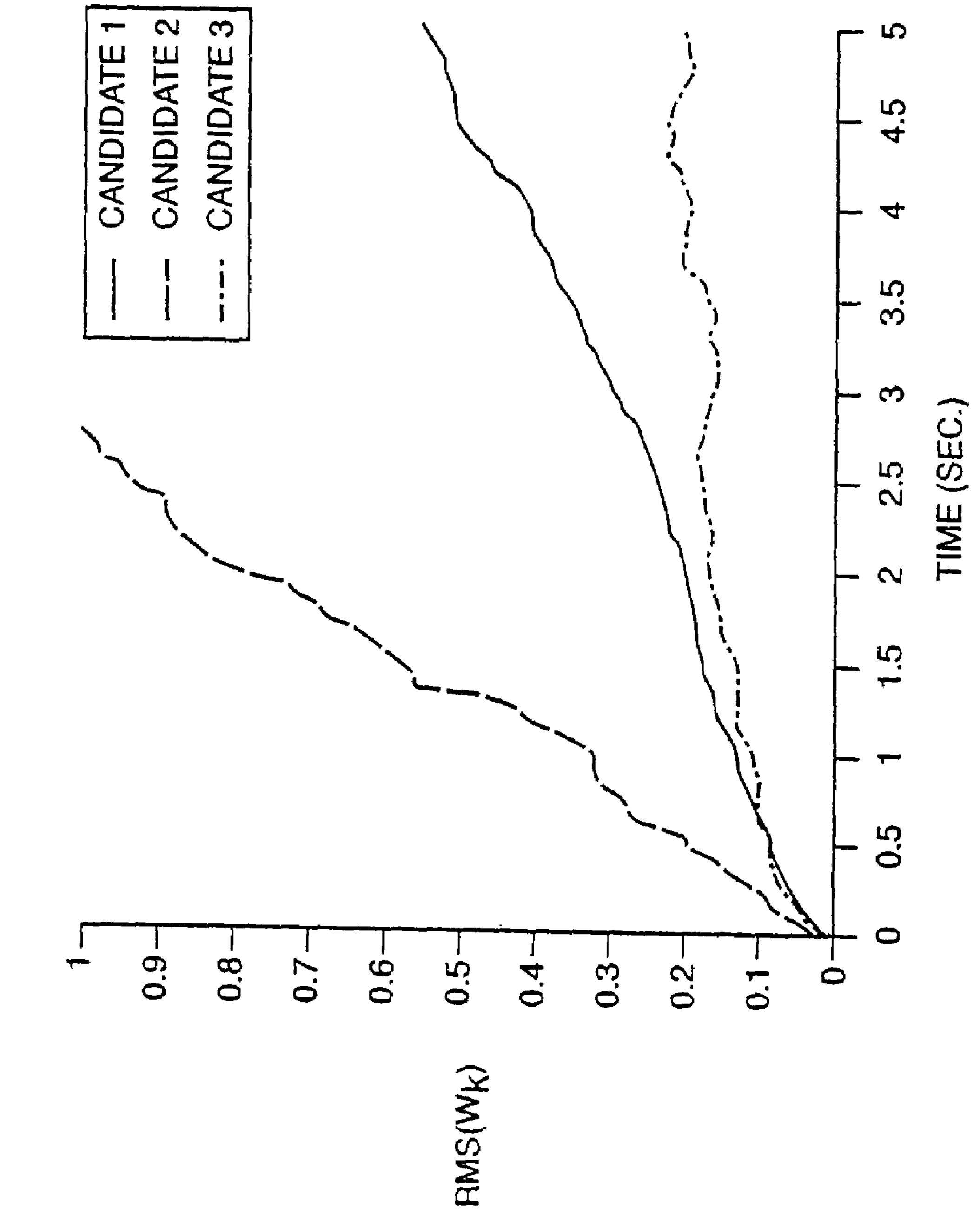
Figure 16:
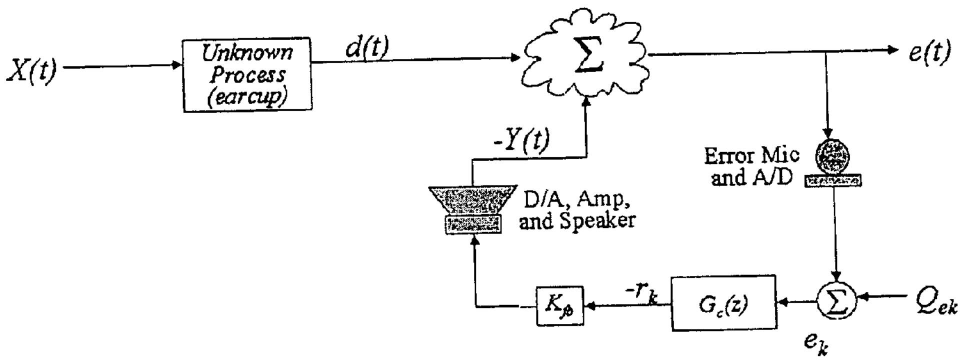
FIG. 16 Prior Art
Figure 17:
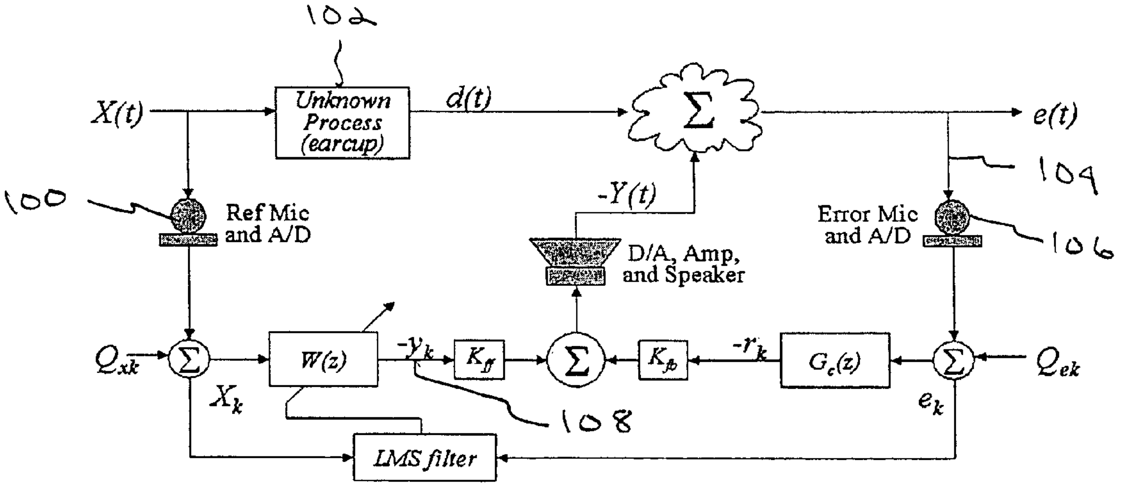
Figure 19:
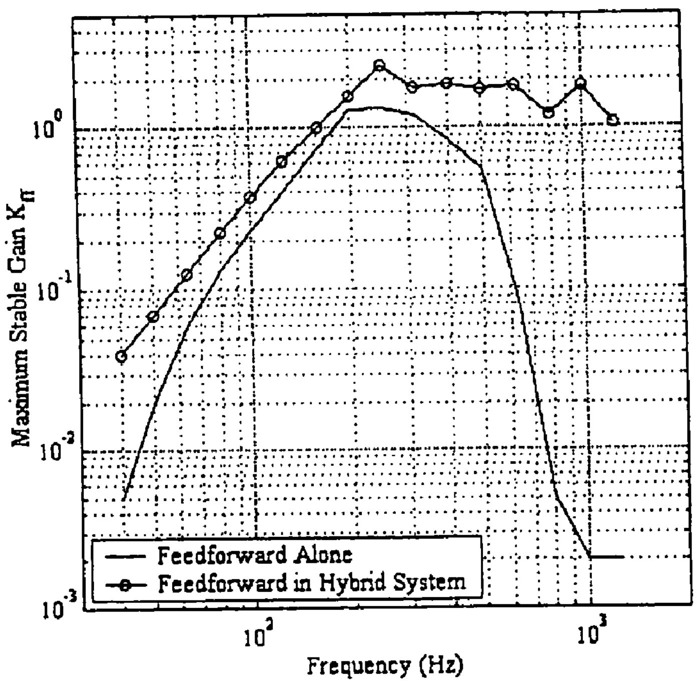
Figure 18:
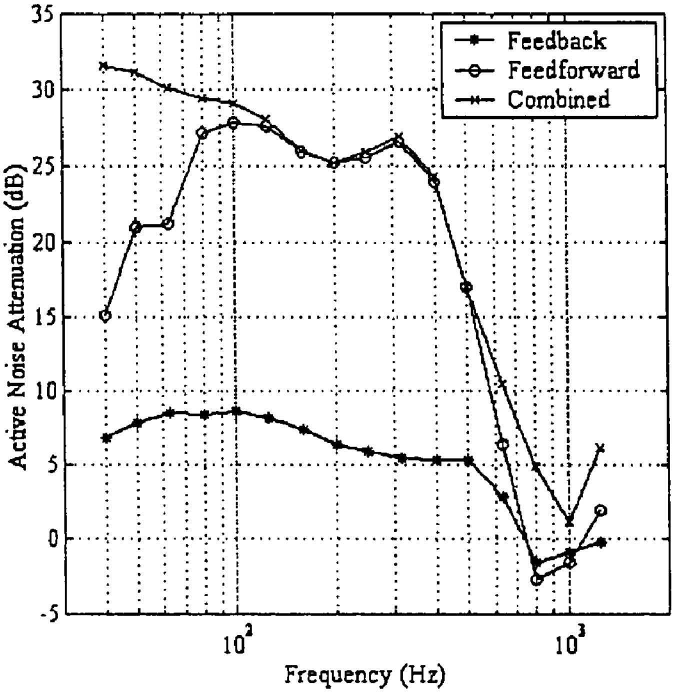

Hz as measured at a microphone mounted approximately at the location of a user's ear, and two headsets, one of which embodies the present invention;

FIG. 5 illustrates the weight error function projected embodiment of the present invention;

FIGS. 6A–6I show plots of a Lyapunov function difference, $V_{k+1}-V_k$, vs. parameters A and B defined in eq. 30 and 31 for signal-to-noise ratio (SNR) of 2, 10, and 100, and a filter length of 20;

FIG. 7 shows numerical results corresponding to the graphs of FIG. 6; and FIG. 8 is a graph of a representative power spectrum of aircraft noise for experimental evaluation of the tuned leaky LMS algorithm of the present invention showing statistically determined upper and lower bounds on the power spectrum and the band limited frequency range used in experimental testing;

FIG. 9 is a table showing the experimentally determined mean tuning parameters for three candidate adaptive LNLMS algorithms;

FIG. 10 is a graph of the performance of empirically tuned NLMS and LNLMS algorithms for nonstationary aircraft noise at 100 dB;

FIG. 11 is a graph of the performance of empirically tuned NLMS and LNLMS algorithms for nonstationary aircraft noise at 80 dB;

FIGS. 12A and 12B show RMS weight vector trajectory for empirically tuned NLMS and LNLMS algorithms for nonstationary aircraft noise at 100 dB SPL and 80 dB SPL respectively;

FIG. 13 is a graph of the performance of three candidate-tuned LNLMS LLMS algorithms for nonstationary aircraft noise as 100 dB in which candidate 1 represents equations 33 and 34, candidate 2 equations 33 and 37, and candidate 3 equations 38 and 43;

FIG. 14 is a graph of the performance of three candidate-tuned LNLMS LLMS algorithms for nonstationary aircraft noise at 80 dB in which candidate 1 represents equations 33 and 34, candidate 2 equations 33 and 37, and candidate 3 equations 38 and 43;

FIG. 15 is a graph showing RMS weight vector histories for both 80 dB and 100 dB SPL;

FIG. 16 is a schematic diagram of the prior art ANR architecture;

FIG. 17 is a schematic diagram of combined feedforward-feedback topology in accordance with one aspect of the present invention;

FIG. 18 is a graph illustrating the active attenuation performance of each individual system/method in response to puretone noise; and FIG. 19 is a graph illustrating experimentally determined maximum stable gains of the disclosed feedforward system and method with and without a feedback component.

DETAILED DESCRIPTION OF THE PREFERRED EMBODIMENTS

Figure 1:
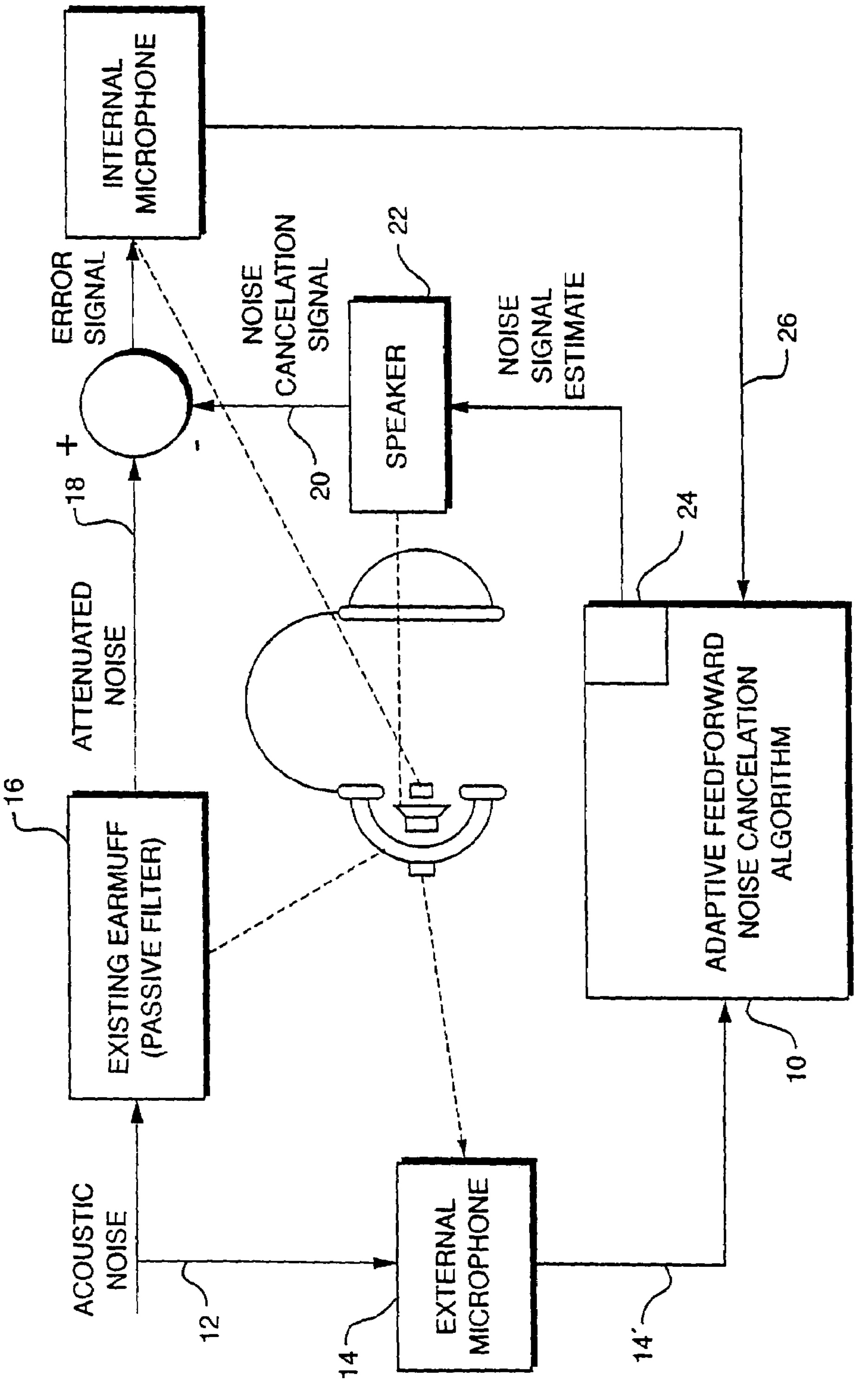
FIG. 1 is block diagram of one implementation of the a system on which the method of tuning an adaptive leaky LMS filter in accordance with the present invention can be practiced.

Operation of the adaptive feedforward LMS algorithm of the present invention is described in conjunction with the block diagram of FIG. 1, which is an embodiment of an adaptive LMS filter 10 in the context of active noise reduction in a communication headset. In a feedforward noise reduction system, the external acoustic noise signal 12, $X_k$, is measured by a microphone 14. The external acoustic noise signal is naturally attenuated passively 16, as it passes through damping material, for example, a headset shell structure, and is absorbed by foam liners within the ear cup of the headset, as defined on [0061].

The attenuated noise signal 18 is then cancelled by an equal and opposite acoustic noise cancellation signal 20, $y_k$, generated using a speaker 22 inside the ear cup of the communication headset. The algorithm 24 that computes $y_k$ is the focus of the present invention. Termed an adaptive feedforward noise cancellation algorithm in the block diagram, it provides the cancellation signal as a function of the measured acoustic noise signal $X_k$ (14'), and the error signal $e_k$ (26), which is a measure of the residual noise after cancellation.

In real-world applications, each of these measured signals contains measurement noise due to microphones and associated electronics and digital quantization. Current embodiments of the adaptive feedforward noise canceling algorithm include two parameters—an adaptive step size $\mu_k$ that governs convergence of the estimated noise cancellation signal, and a leakage parameter λ. The traditional normalized, leaky feedforward LMS algorithm is given by the following two equations:

$$y_k = W_k^T X_k$$

$$W_{k+1} = \lambda W_k + \mu_k X_k e_k \qquad (1, 2)$$

wherein $W_k$ is a weight vector, or set of coefficients of a finite-impulse response filter. λ=1 for ideal conditions: no measurement noise; no quantization noise; deterministic and statistically stationary acoustic inputs; discrete frequency components in $X_k$; and infinite precision arithmetic. Under these ideal conditions, the filter coefficients converge to those required to minimize the mean-squared $e_k$.

Algorithms for selecting parameter $\mu_k$ appear in the literature and modifications or embodiments of published $\mu_k$ selection algorithms appear in various prior art. However, the choice of parameters λ and $\mu_k$ as presented in the prior art does not guarantee stability of the traditional LMS algorithm under non-ideal real-world conditions, in which measurement noise in the microphone signals is present, finite precision effects reduce the accuracy of numerical computations, and noise fields are highly nonstationary.

Furthermore, in current algorithms, the leakage parameter must be selected so as to maintain stability for worst case, i.e., nonstationary noise fields with impulsive noise content, resulting in significant noise cancellation degradation. Parameter λ is a constant between zero and one. Choosing λ=1 results in aggressive performance, with compromised stability under real-world conditions. Choosing λ<1 enhances stability at the expense of performance, as the algorithm operates far away from the optimal solution.

The invention disclosed here is a computational method, based on a Lyapunov tuning approach, and its embodiment that automatically tunes time varying parameters $\lambda_k$ and $\mu_k$ so as to maximize stability with minimal reduction in performance under noise conditions with persistent or periodic low signal-to-noise ratio, low excitation levels, and nonstationary noise fields. The automatic tuning method provides for time-varying tuning parameters $\lambda_k$ and $\mu_k$ that are functions of the instantaneous measured acoustic noise signal $X_k$, weight vector length, and measurement noise variance.

The adaptive tuning law that arises from the Lyapunov tuning approach that has been tested experimentally is as follows:

$$\mu_k = \frac{\mu_o \lambda_k}{(X_k + Q_k)^T (X_k + Q_k)} \quad (3)$$

$$\lambda_k = \frac{(X_k + Q_k)^T (X_k + Q_k) - 2L\sigma_q^2}{(X_k + Q_k)^T (X_k + Q_k)} \quad (4)$$

wherein $X_k+Q_k$ is the measured reference signal, which contains measurement noise $Q_k$ due to electronic noise and quantization. The measurement noise is of known variance $\sigma_q^2$. L is the length of weight vector $W_k$. This choice of tuning parameters provides maximal stability and performance of the leaky LMS algorithm, causing it to operate at small leakage factors only when necessary to preserve stability, while providing mean leakage factors near unity to maximize performance. Through application of these adaptive tuning parameters developed using the Lyapunov tuning approach, continual updating of the tuning parameters preserves stability and performance in non-ideal, real world noise fields described in [0005].

Summary of Experimental Results

Three candidate tuning laws that result from the Lyapunov tuning approach of the invention have been implemented and tested experimentally for low frequency noise cancellation in a prototype communication headset. The prototype headset consists of a shell from a commercial headset, which has been modified to include ANR hardware components, i.e., an internal error sensing microphone, a cancellation speaker, and an external reference noise sensing microphone. For experimental evaluation of the ANR prototype headset, the tuning method of the present invention is embodied as software within a commercial DSP system, the dSPACE DS 1103.

Figure 2:
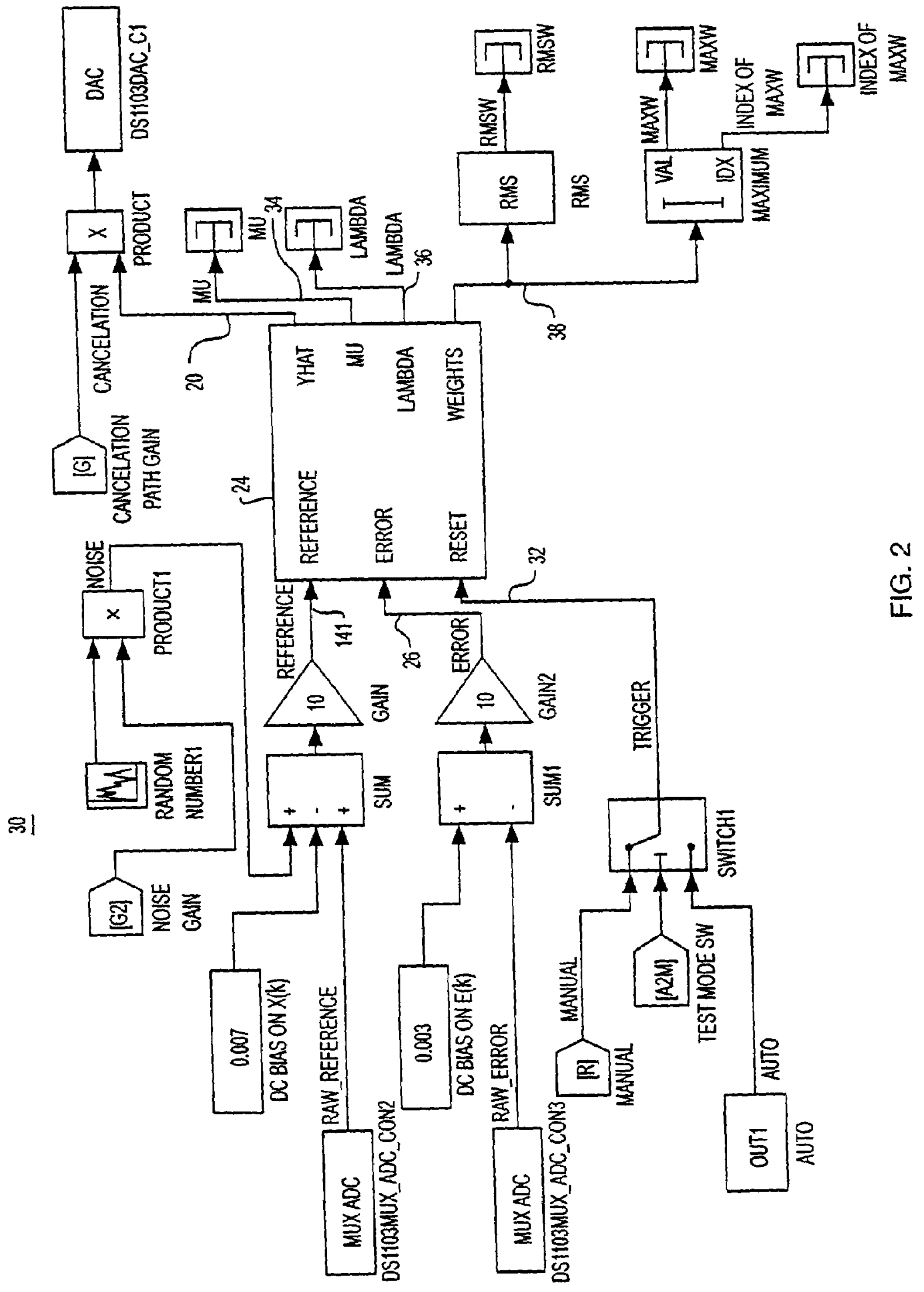
FIG. 2 is schematic view of the experimental embodiment of the disclosed invention.

A block diagram 30, FIG. 2, shows one implementation of the present invention. The preferred embodiment of the 'Adaptive Leaky LMS' 24 contains a c-program that embodies the tuning method of the present invention, although a software implementation is not specific to nor a limitation of the present invention, but is applicable to all feedforward adaptive noise cancellation system embodiments. The three inputs to the Adaptive Leaky LMS block are the reference noise 14', the error microphone 26, and a 'reset' trigger 32 that is implemented for experimental analysis. The output signals are the acoustic noise cancellation signal 20, the tuned parameters $\lambda_k$ (34) and $\mu_k$ (36), and the filter coefficients 38.

The stability and performance of the resulting Active Noise Reduction (ANR) system has been investigated for a variety of noise sources ranging from deterministic discrete frequency components (pure tones) and stationary white noise to highly nonstationary measured F-16 aircraft noise over a 20 dB dynamic range. Results demonstrate significant improvements in stability of the adaptive leaky LMS algorithm disclosed (Eq. 3–4) over traditional leaky or non-leaky normalized algorithms, while providing noise reduction performance equivalent to that of a traditional NLMS algorithm for idealized noise fields. Performance comparisons have been made as a function of signal-to-noise ratio (SNR) as well, showing a substantial improvement in ANR performance at low SNR.

Figure 3:
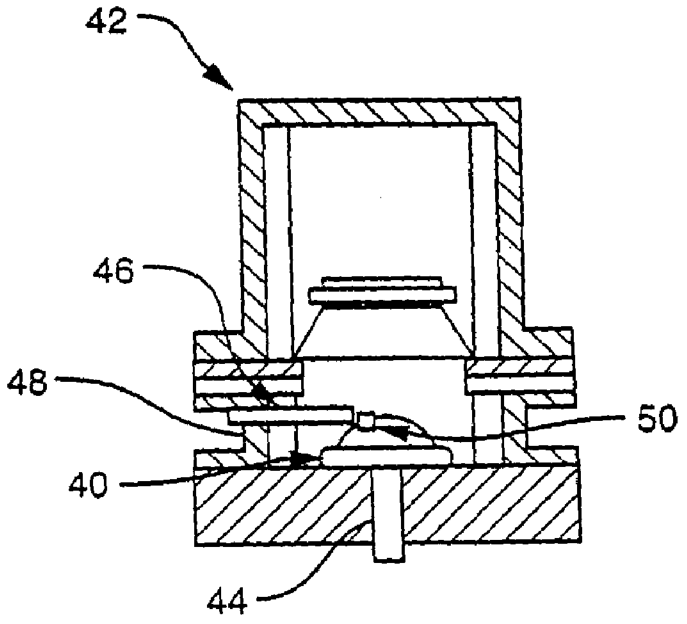
FIG. 3 is a schematic view of a test cell utilized for verifying the experimental results of the present invention.

Performance of the prototype communication headset ANR system 40, FIG. 3, employing the disclosed tuning method has been experimentally compared with a commercial electronic noise cancellation headset that uses a traditional feedback ANR algorithm. Both headsets were evaluated within a low frequency test cell 42 specifically designed to provide a highly controlled and uniform acoustic environment.

To perform the evaluation, a calibrated B&K microphone 44 was placed in the base of the test cell 42. A Larson-Davis calibrated microphone 46 with a wind boot was placed in the side 48 of the test cell 42, approximately 0.25 inches from the external reference noise microphone 50 of the headset 40 under evaluation. The Larson Davis microphone 46 measured the sound pressure level of the external noise when the headset 40 is in the test cell 42. The B&K microphone 44, which was mounted approximately at the location of a user's ear, was used to record sound pressure level (SPL) attenuation performance. With this test setup, each headset was subject to a sum of pure tones at 50, 63, 80, 100, 125, 160, and 200 Hz and 100 dB SPL. Both the passive attenuation and total attenuation were measured.

Figure 4A:
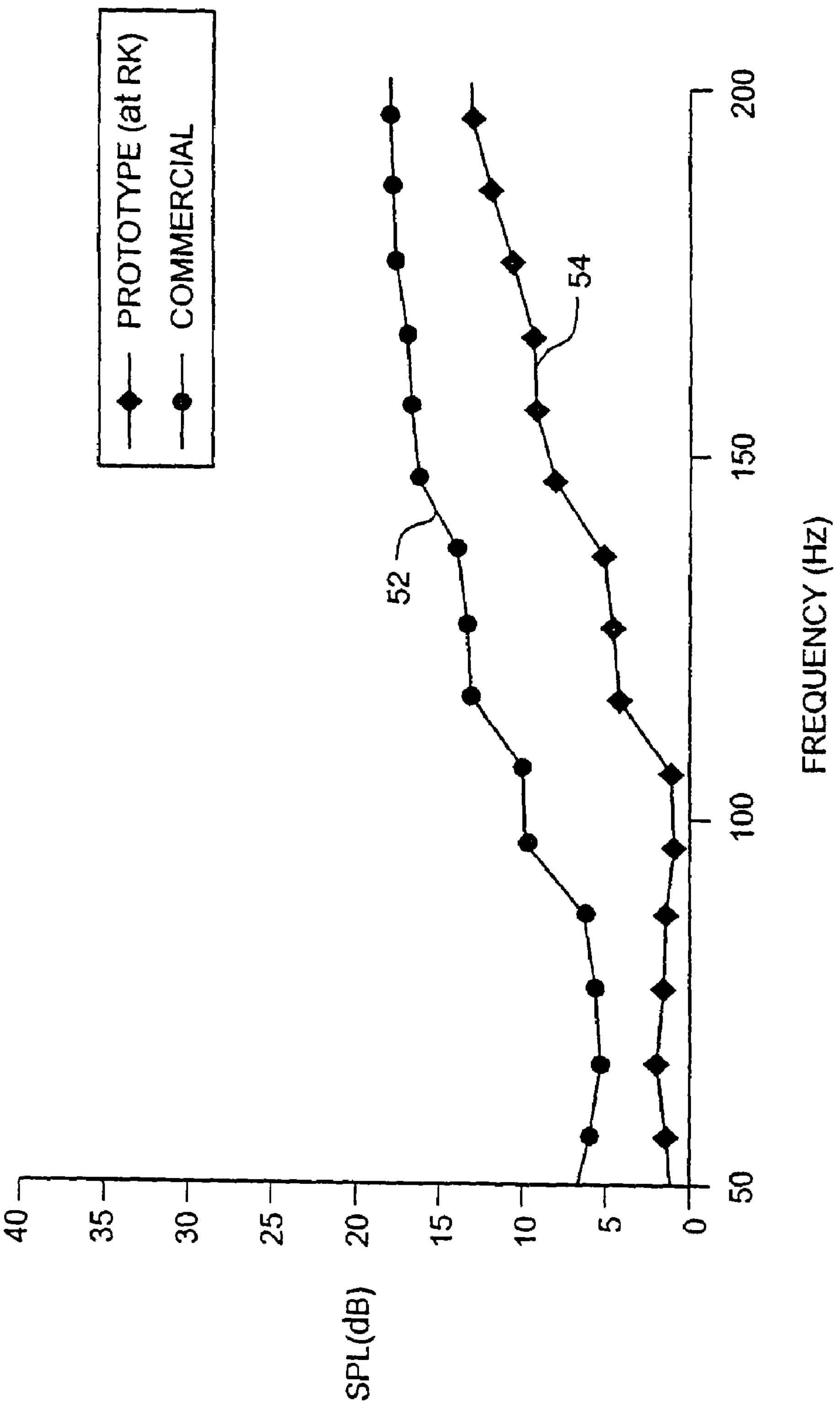
FIGS. 4A and 4B are graphs showing active and passive SPL attenuation for a sum of pure tones between 50 and 200
Figure 4B:
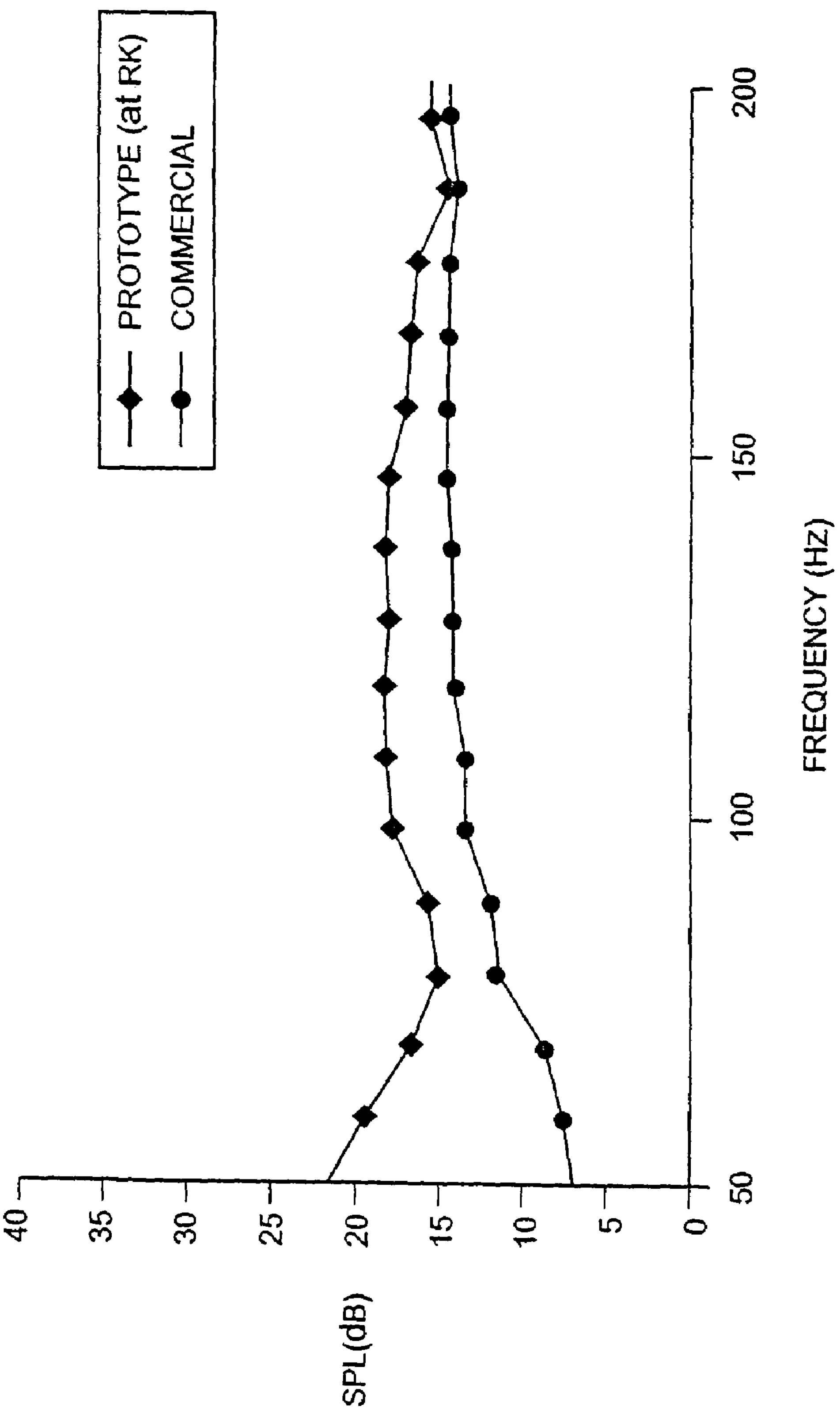
Figure 6A:
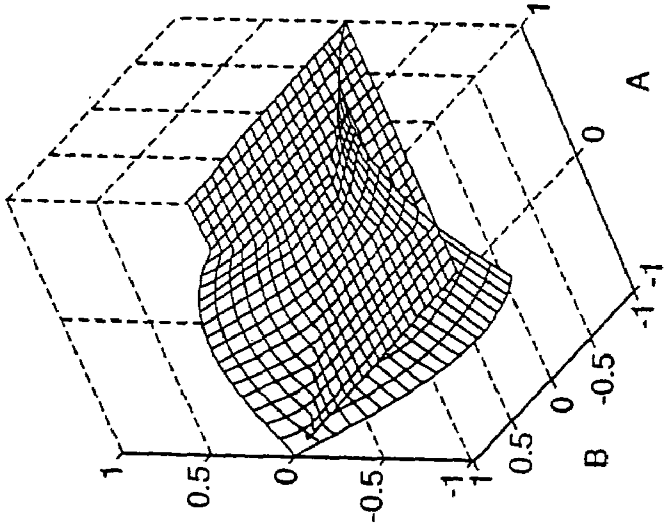
Figure 6B:
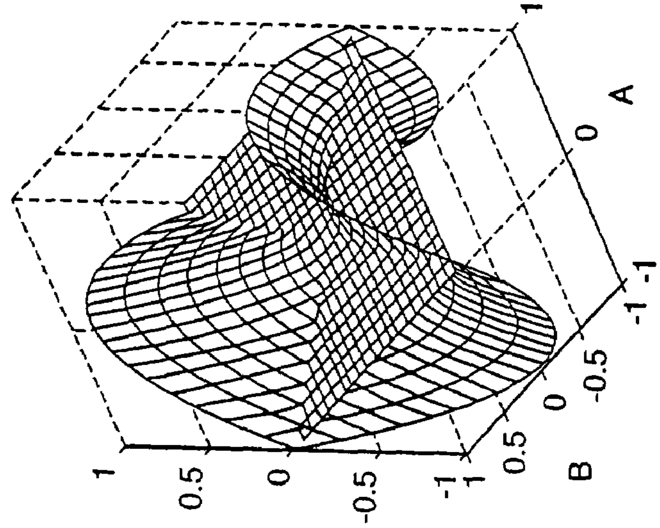
Figure 6C:
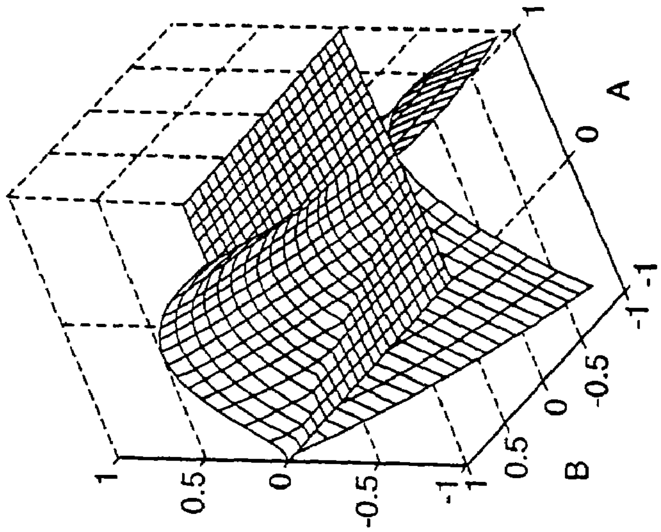
Figure 6D:
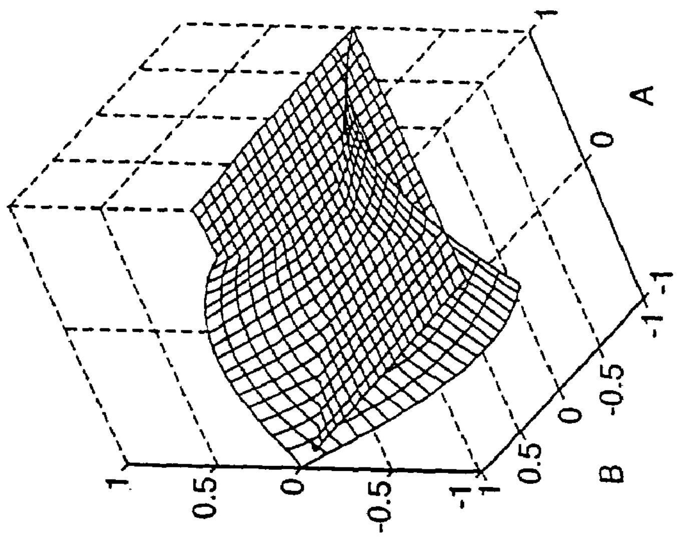
Figure 6E:
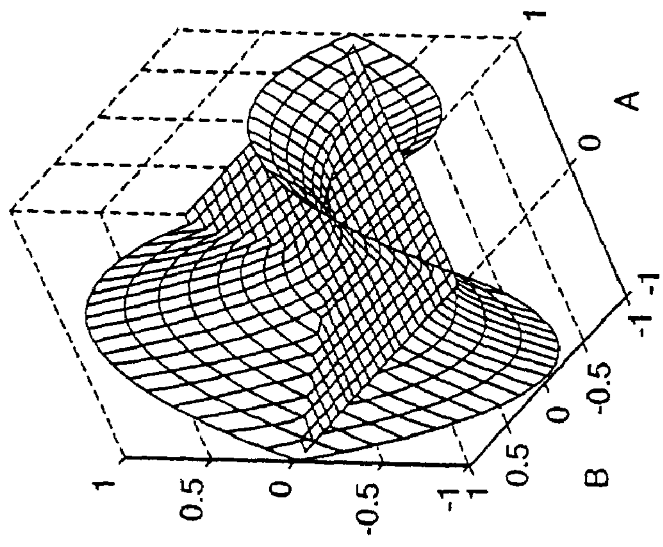
Figure 6F:
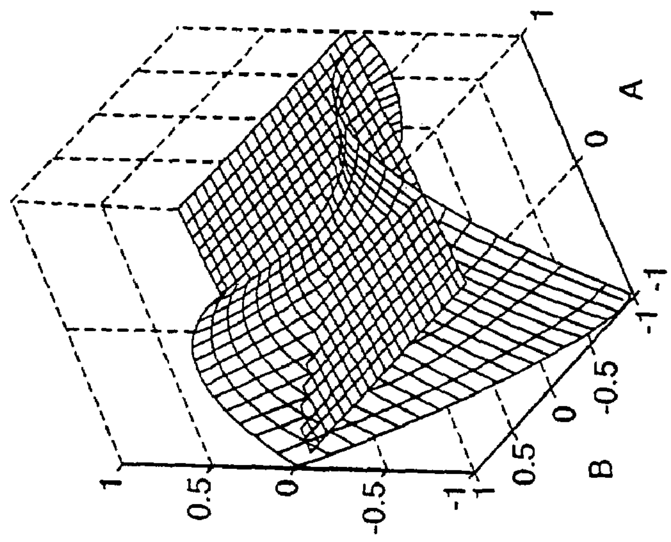
Figure 6G:
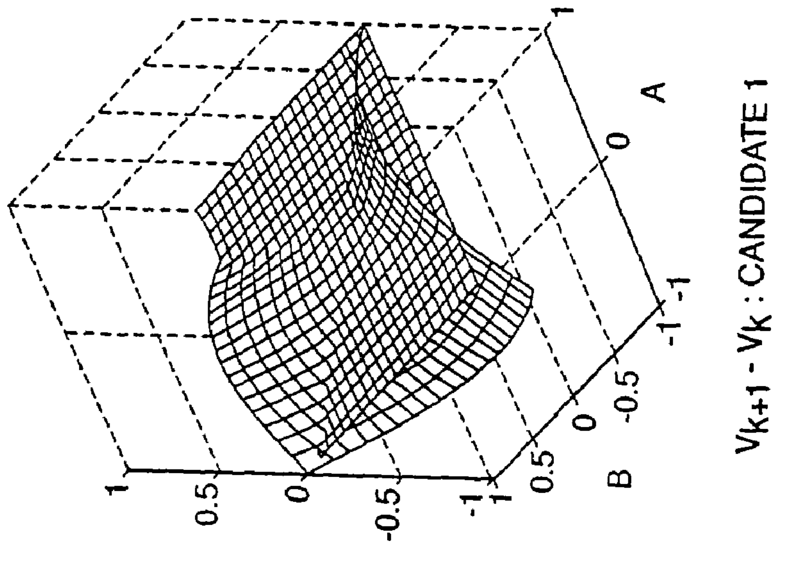
Figure 6H:
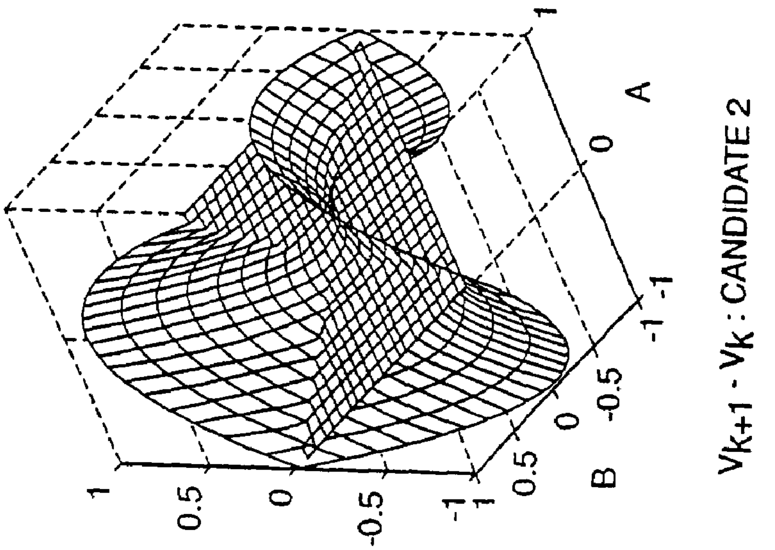
Figure 6I:
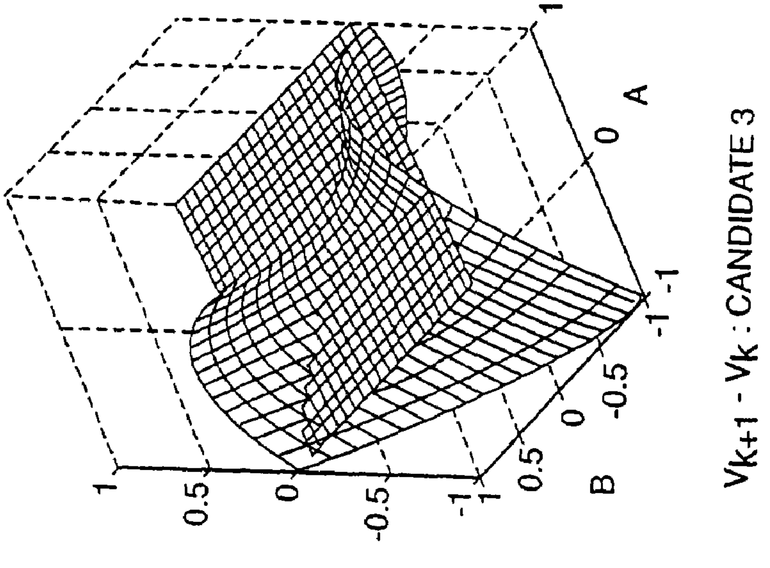

The active and passive attenuation of each headset, as measured by the power spectrum of the difference between the external Larson-Davis microphone 46 and internal B&K microphone 44 is recorded in FIG. 4A and 4B respectively. The ANR prototype headset that uses the disclosed automatic tuning algorithm achieves superior active SPL attenuation at all frequencies in the 50–200 Hz band as measured at the B&K microphone 44. Passive noise attenuation of the commercial headset 52 is superior to the prototype headset 54, which being a prototype, was not optimized for passive performance.

These measured results demonstrate that a headset with the combination of current technology in passive performance, and the superior active performance provided by the disclosed tuning method can achieve 30–35 dB SPL attenuation of low frequency stationary noise at the ear over the 50 to 200 Hz frequency band. This is a significant improvement over commercially available electronic feedback noise cancellation technology. There is both a theoretical and experimental basis for extending this performance over a wider frequency range. Additional test results are discussed below.

Review of the Leaky Least Mean Square (LMS) Algorithm

A review of the LMS algorithm and its leaky variant follows. Denoting $X_k \epsilon R^n$ as the reference input at time $t_k$ and $d_k \epsilon R^1$ as the output of the unknown process, the LMS algorithm recursively selects a weight vector $W_k \epsilon R^n$ to minimize the squared error between $d_k$ and the adaptive filter output $W_k^T X_k$.

The cost function is $$J = \frac{1}{2} e_k^2 \quad (5)$$

where $$e_k = d_k - W_k^T X_k. \quad (6)$$

The well-known Wiener solution, or optimum weight vector is $$W_o = E[X_k X_k^T]^{-1} E[X_k d_k] \quad (7)$$

where $E[X_k X_k^T]$ is the autocorrelation of the input signal and $E[X_k d_k]$ is the cross correlation between the input vector and process output. The Wiener solution reproduces the unknown process, such that $d_k=W_o^T X_k$.

By following the stochastic gradient of the cost surface, the well-known unbiased, recursive LMS solution is obtained:

$$W_{k+1}=W_k+\mu e_k X_k \tag{8}$$

Stability, convergence, and random noise in the weight vector at convergence are governed by the step size $\mu$. Fastest convergence to the Wiener solution is obtained for $$\mu=\frac{1}{\lambda_{\max}}$$

where $\lambda_{max}$ is the largest eigenvalue of the autocorrelation matrix $E[X_k X_k^T]$.

As an adaptive noise cancellation method, LMS has some drawbacks. First, high input power leads to large weight updates and large excess mean-square error at convergence. Operating at the largest possible step size enhances convergence, but also causes large excess mean-square error, or noise in the weight vector, at convergence. A nonstationary input dictates a large adaptive step size for enhanced tracking, thus the LMS algorithm is not guaranteed to converge for nonstationary inputs.

In addition, real world applications necessitate the use of finite precision components, and under such conditions, the LMS algorithm does not always converge in the traditional form of eq. 4, even with an appropriate adaptive step size. Finally, nonpersistent excitation due to a constant or nearly constant reference input, such as can be the case during 'quiet periods' in adaptive noise cancellation systems with nonstationary inputs, can also cause weight drift.

In response to such issues, the leaky LMS (LLMS) algorithm or step-size normalized versions of the leaky LMS algorithm "leak off" excess energy associated with weight drift by including a constraint on output power in the cost function to be minimized. Minimizing the resulting cost function, $$J=\frac{e_k^2+\gamma W_k^T W_k}{2} \tag{9}$$

results in the recursive weight update equation $$W_{k+1}=\lambda W_k+\mu e_k X_k \tag{10}$$

where $\lambda=1-\gamma\mu$ is the leakage factor. Under conditions of constant tuning parameters $\lambda$ and $\mu$, no measurement noise or finite-precision effects, and bounded signals $X_k$ and $e_k$, eq. 6 converges to:

$$W_k=\sum_{i=0}^{k-1}\lambda^i \mu X_{k-1-i} e_{k-1-i} \tag{11}$$

as $k\to\infty$. Thus, for stability $0\leqq\lambda\leqq 1$ is required. The lower bound on $\lambda$ assures that the sign of the weight vector does not change with each iteration.

The traditional constant leakage factor leaky LMS results in a biased weight vector that does not converge to the Wiener solution and hence results in reduced performance over the traditional LMS algorithm and its step size normalized variants.

The prior art documents a 60 dB decrease in performance for a simulated a leaky LMS over a standard LMS algorithm when operating under persistently exciting conditions. Hence, the need is to find time varying tuning parameters that maintain stability and retain maximum performance of the leaky LMS algorithm in the presence of quantifiable measurement noise and bounded dynamic range.

Lyapunov Tuning of the Leakage Factor

In the presence of measurement noise $Q_k \in R^n$ corrupting the reference signal $X_k$, and with time varying leakage and step size parameters, $\lambda_k$ and $\mu_k$, the LLMS weight update equation becomes $$W_{k+1}=\lambda_k W_k+\mu_k(W_o^T X_k-W_k^T(X_k+Q_k))(X_k+Q_k) \tag{12}$$

The stability analysis objective is to find operating bounds on the variable leakage parameter $\lambda_k$ and the adaptive step size $\mu_k$ to maintain stability in the presence of noise vector $Q_k$ whose elements have known variance, given the dynamic range or a lower bound on the signal-to-noise ratio.

For stability at maximal performance, the present invention seeks time-varying parameters $\lambda_k$ and $\mu_k$ such that certain stability conditions on a candidate Lyapunov function $V_k$ are satisfied for all k in the presence of quantifiable noise on reference input $X_k$. Moreover, the choice of $\lambda_k$ and $\mu_k$ should be dependent on measurable quantities, such that a parameter selection algorithm can be implemented in real-time. Finally, the selection algorithm should be computationally efficient. For uniform asymptotic stability, the Lyapunov stability conditions are:

$$\text{i) } V_k\geqq 0 \tag{13}$$

$$\text{ii) } V_{k+1}-V_k<0 \tag{14}$$

and a decrescent Lyapunov function is required, i.e., $V_k=0$ at $W_k=0$, and $V_k<V^*$ for all $k\geqq 0$, where $V^*$ is a time-invariant scalar function of $W_k$. Finally, for global uniform asymptotic stability, the scalar function $V^*$ must be radially unbounded, such that $$\text{iii) } \lim_{\tilde{w}_k\to\infty} V_k=\infty \tag{15}$$

Development of the candidate Lyapunov function proceeds by first defining $W_k=W_k-W_o$. Eq. 12 becomes $$W_{k+1}=(\lambda_k I-\mu_k(X_k+Q_k)(X_k+Q_k)^T) W_k+(\lambda_k I-I-\mu_k(X_k+Q_k)Q_k^T)W_o \tag{16}$$

Since scalar tuning parameters $\lambda_k$ and $\mu_k$ are required, $W_k$ and $W_{k+1}$ are projected in the direction of $X_k+Q_k$, as shown in FIG. 5:

$$\tilde{w}_k=\tilde{W}_k^T\frac{X_k+Q_k}{\|X_k+Q_k\|} \tag{17}$$

$$\tilde{w}_{k+1}=\tilde{W}_{k+1}^T\frac{X_k+Q_k}{\|X_k+Q_k\|} \tag{18}$$

Combining Eq. 16 through 18 and simplifying the expression gives $$\tilde{w}_{k+1} = \tilde{W}_k^T(\lambda_k - \mu_k\|X_k + Q_k\|^2)\frac{X_k + Q_k}{\|X_k + Q_k\|} + W_o^T\left((\lambda_k - 1)\frac{X_k + Q_k}{\|X_k + Q_k\|} - \mu_k Q_k\|X_k + Q_k\|\right) \quad (19)$$

A candidate Lyapunov function satisfying stability condition i) above (Eq. 13), is $$V_k = \tilde{w}_k^T \tilde{w}_k \quad (20)$$

thus the Lyapunov function difference is $$V_{k+1} - V_k = \tilde{w}_{k+1}^T \tilde{w}_{k+1} - \tilde{w}_k^T \tilde{w}_k \quad (21)$$

The expression for the projected weight update in Eq. 19 can be simplified as $$\tilde{w}_{k+1} = (\phi_k W_k + \gamma_{1_k} W_o)^T u_k + \gamma_{2_k} W_o^T \alpha_k \quad (22)$$

where $$u_k = \frac{(X_k + Q_k)}{|X_k + Q_k|} \quad (23)$$

is the unit vector in the direction of $X_k+Q_k$, and $$\phi_k = \lambda_k - \mu_k (X_k + Q_k)^T (X_k + Q_k) \quad (24)$$

$$\gamma_{1_k} = \lambda_k - 1 \quad (25)$$

$$\gamma_{2_k} = -\mu_k (X_k + Q_k)^T (X_k + Q_k) \quad (26)$$

$$\alpha_k = \frac{Q_k}{\|X_k + Q_k\|} \quad (27)$$

With these definitions, the Lyapunov function difference becomes, $$V_{k+1} - V_k = (\phi_k^2 - 1)\tilde{W}_k^T u_k u_k^T \tilde{W}_k + \gamma_{1_k}^2 W_o^T u_k u_k^T W_o + \gamma_{2_k}^2 W_o^T \alpha_k \alpha_k^T W_o + 2\phi_k \gamma_{1_k} \tilde{W}_k^T u_k u_k^T W_o + 2\phi_k \gamma_{2_k} \tilde{W}_k^T u_k \alpha_k^T W_o + 2\gamma_{1_k}\gamma_{2_k} W_o^T u_k \alpha_k^T W_o \quad (28)$$

Note that the projected weight vector of Eq. 17 and 18 and the resulting Lyapunov function candidate of Eq. 20 do not satisfy condition Lyapunov stability condition iii) (Eq. 15), which is required for global uniform asymptotic stability. However, it is possible to find a time-invariant scalar function V* such that the Lyapunov candidate $V_k < V^*$ for all k>0.

Since the scalar projection is always in the direction of the unit vector defined by eq. 16, an example of such a function is $V^* = 10\tilde{W}_k^T \tilde{W}_k$. Hence, the Lyapunov function can be used to assess uniform asymptotic stability.

Note also that there are two conditions that may be considered problematic with the projected weight vector. These occur if (a) $X_k = -Q_k$ or (b) $\tilde{W}_k$ is orthogonal to $u_k$ or some component of $\tilde{W}_k$ is orthogonal to $u_k$. Condition (a) is highly unlikely, especially at realistic tap lengths and signal-to-noise ratios (SNR). In fact, if this condition does occur, then, intuitively, it must be the case that SNR is so low that noise cancellation is futile, since the noise floor effectively dictates the maximum performance that can be achieved.

If $\tilde{W}_k$ is orthogonal to $u_k$ under reasonable SNR conditions, then it is likely that the filter output $e_k$ is very close to zero, i.e., the LMS algorithm is simply unnecessary if such a condition persists. Thus, though it is possible, but unlikely, that one or more of the weight vector components could become unbounded, in considering such unlikely occurrences it is impossible to avoid serious performance degradation.

The goal of the Lyapunov analysis is to enable quantitative comparison of stability and performance tradeoffs for candidate tuning rules. Since uniform asymptotic stability suffices to make such comparisons, and since the Lyapunov function of Eq. 20 enhances the ability to make such comparisons, it was selected for the analysis that follows.

Several approaches to examining Lyapunov stability condition ii) $V_{k+1} - V_k < 0$ for Eq. 28 exist. The usual approach to determining stability is to examine $V_{k+1} - V_k$ term by term to determine whether the two parameters $\lambda_k$ and $\mu_k$ can be chosen to make each term negative thereby guaranteeing uniform asymptotic stability. Since there are several terms that are clearly positive in Eq. 28, there is no guarantee that each individual term will be negative. Furthermore, it is clear from an analysis of Eq. 28 that the solution is nearly always biased away from zero. At $\tilde{W}_k = W_k - W_o = 0$, Eq. 28 becomes:

$$V_{k+1} - V_k = \gamma_{1_k}^2 W_o^T u_k u_k^T W_o + \gamma_{2_k}^2 W_o^T \alpha_k \alpha_k^T W_o + 2\gamma_{1_k}\gamma_{2_k} W_o^T u_k \alpha_k^T W_o \quad (29)$$

For $0 < \lambda_k < 1$, all coefficients of terms in Eq. 29 are positive, and it is clear that a negative definite $V_{k+1} - V_k$ results only if $\gamma_{1_k}^2 W_o^T u_k u_k^T W_o + \gamma_{2_k}^2 W_o^T \alpha_k \alpha_k^T W_o < -2\gamma_{1_k}\gamma_{2_k} W_o^T u_k \alpha_k^T W_o$ with $\gamma_{1_k}\gamma_{2_k} > 0$. That the leaky LMS algorithm, as examined using the Lyapunov candidate of Eq. 20, is biased away from $W_o$ is in agreement with the prior art. It is possible, but difficult, to examine the remaining space of $\tilde{W}_k = W_k - W_o$ (i.e., the space that excludes the origin) to determine whether time varying tuning parameters can be found to guarantee stability of some or all other points in the space or a maximal region of the space.

Time varying tuning parameters are required since constant tuning parameters found in such a manner will retain stability of points in the space at the expense of performance. However, since we seek time varying leakage and step size parameters that are uniquely related to measurable quantities and since the Wiener solution is generally not known a priori, the value of such a direct analysis of the remaining space of $\tilde{W}_k = W_k - W_o$ is limited.

Thus, the approach taken in the present invention is to define the region of stability around the Wiener solution in terms of parameters:

$$A = \frac{\tilde{W}_k^T u_k}{W_o^T u_k} \quad (30)$$

$$B = \frac{W_o^T \alpha_k}{W_o^T u_k} \quad (31)$$

and to parameterize the resulting Lyapunov function difference such that the remaining scalar parameter(s) can be chosen by optimization.

The parameters A and B physically represent the output error ratio between the actual output and ideal output for a system converged to the Wiener solution, and the output noise ratio, or portion of the ideal output that is due to noise vector $Q_k$. Physically, these parameters are inherently statistically bounded based on i) the maximum output that a real system is capable of producing, ii) signal-to-noise ratio in the system, and iii) the convergence behavior of the system. Such bounds can be approximated using computer simulation. These parameters provide convenient means for visualizing the region of stability around the Wiener solution and thus for comparing candidate tuning rules.

In a persistently excited system with high signal-to-noise ratio, B approaches zero, while the Wiener solution corresponds to A=0, i.e., $W_k=W_o$. Thus, high performance and high SNR operating conditions imply both A and B are near zero in the leaky LMS algorithm, though the leaky solution will always be biased away from A=0. In a system with low excitation and/or low signal-to-noise ratio, larger instantaneous magnitudes of A and B are possible, but it is improbable that the magnitude of either A or B is >>1 in practice. Note that B depends only on the reference and noise vectors, and thus it cannot be influenced by the choice of tuning parameters. B can, however, affect system stability.

Using parameters A and B, Eq. 28 becomes $$V_{k+1}-V_k = \left((\phi_k^2-1)A^2+\gamma_{1_k}^2+\gamma_{2_k}^2B^2+2\phi_k\gamma_{1_k}A+2\phi_k\gamma_{2_k}AB+2\gamma_{1_k}\gamma_{2_k}B\right) W_o^T u_k u_k^T W_o \quad (32)$$

By choosing an adaptive step size and/or leakage parameter that simplifies analysis of Eq. 32, one can parameterize and subsequently determine conditions on remaining scalar parameters such that $V_{k+1}-V_k<0$ for the largest region possible around the Wiener solution. Such a region is now defined by parameters A and B, providing a means to graphically display the stable region and to visualize performance/stability tradeoffs introduced for candidate leakage and step size parameters.

Comparison of Candidate Tuning Laws Using Lyapunov Analysis

To demonstrate the use of the parameterized Lyapunov difference of Eq. 32, consider three candidate leakage parameter and adaptive step size combinations.

The first candidate uses a traditional choice for leakage parameter in combination with a traditional choice for adaptive step size to provide:

$$\lambda_k=1-\mu_k\sigma_q^2 \quad (33)$$

$$\mu_k = \frac{\mu_0}{(X_k+Q_k)^T(X_k+Q_k)} \quad (34)$$

wherein $\sigma_q^2$ is the variance of quantifiable noise corrupting each component of vector $X_k$. This choice results in a simple relationship for the constants in Eq. 32

$$\phi_k=\lambda_k-\mu_o \quad (35)$$

$$\gamma_{2_k}=-\mu_o \quad (36)$$

Thus, the combined candidate step size and leakage factor parameterize Eq. 32 in terms of $\mu_o$.

To determine the optimal $\mu_o$, one can perform a scalar optimization of $V_{k+1}-V_k$ with respect to $\mu_o$ and evaluate the result for worst-case constants A and B. In essence, one seeks the value of $\mu_o$ that makes $V_{k+1}-V_k$ most negative for worst-case deviations of weight vector $W_k$ from the Wiener solution and for worst-case effects of measurement noise $Q_k$. Worst case A and B are chosen to be that combination in the range $A_{min}\leqq A<0$ and $0<A\leqq A_{max}$, $B_{min}\leqq B\leqq B_{max}$ that provides the smallest (i.e., most conservative) step size parameter $\mu_o$.

For example, for $A_{min}=B_{min}=-1$ and $A_{max}=B_{max}=1$, and the traditional adaptive leakage parameter and step size combination of Eq. 33 and 34, this optimization procedure results in $\mu_o=1/3$, which is consistent with the choice for $\mu_o$.

The second candidate also retains the traditional leakage factor of Eq. 34, and finds an expression for $\mu_k$ as a function of the measured reference input and noise covariance directly by performing a scalar optimization of $V_{k+1}-V_k$ with respect to $\mu_k$. Again, the results are evaluated for worst-case conditions on A and B, as described above. This scalar optimization results in $$\mu_k = \frac{2(X_k+Q_k)^T(X_k+Q_k)+4\sigma_q^2}{2((X_k+Q_k)^T(X_k+Q_k))^2+8\sigma_q^2(X_k+Q_k)^T(X_k+Q_k)+8\sigma_q^4} \quad (37)$$

The final candidate appeals to the structure of Eq. 32 to determine an alternate parameterization as a function of $\mu_o$. Selecting $$\mu_k = \frac{\mu_o\lambda_k}{(X_k+Q_k)^T(X_k+Q_k)} \quad (38)$$

$$\lambda_k = \frac{X_k^TX_k-Q_k^TQ_k}{(X_k+Q_k)^T(X_k+Q_k)} \quad (39)$$

results in $$\phi_k=(1-\mu_o)\lambda_k \quad (40)$$

$$\gamma_{2_k}=-\mu_o\lambda_k \quad (41)$$

$$\gamma_{1_k}=\lambda_k-1 \quad (42)$$

The expression for $\lambda_k$ in Eq. 39 is not measurable, but it can be approximated as $$\lambda_k = \frac{(X_k+Q_k)^T(X_k+Q_k)-2L\sigma_q^2}{(X_k+Q_k)^T(X_k+Q_k)} \quad (43)$$

wherein L is the filter length.

Equation 43 is a function of statistical and measurable quantities, and is a good approximation of Eq. 39 when $\|X_k\|>>\|Q_k\|$. The corresponding definitions of $\phi_k$, $\gamma_{1_k}$, $\gamma_{2_k}$, and $\mu_k$, Eq. 32 becomes $$V_{k+1}-V_k = \begin{pmatrix} (\mu_o\lambda_k)^2(A+B)^2-2\mu_o\lambda_k^2(A^2+A+B+AB)+ \\ (\lambda_k^2-1)A^2+(\lambda_k-1)^2+(\lambda_k^2-\lambda_k)2A+2\mu_o\lambda_k(A+B) \end{pmatrix} W_o^T u_k u_k^T W_o \quad (44)$$

The optimum $\mu_o$ for this candidate, which is again found by scalar optimization subject to worst case conditions on A and B is $\mu_o=1/2$.

In summary, the three candidate adaptive leakage factor and step size solutions are Candidate 1: Eq. 33 and 34, Candidate 2: Eq. 33 and 37, and Candidate 3: Eq. 38 and 43. All are computationally efficient, requiring little additional computation over a fixed leakage, normalized LMS algorithm, and all three candidate tuning laws can be implemented based on knowledge of the measured, noise corrupted reference input, the variance of the measurement noise, and the filter length.

To evaluate stability and performance tradeoffs, one examines $V_{k+1}-V_k$ for various instantaneous signal-to-noise ratios $|X_k|/|Q_k|$ (SNR), and $1>A>-1$, $1>B>-1$.

FIG. 6 shows plots of $V_{k+1}-V_k$ vs. A and B for SNR of 2, (FIGS. 6A–6C) 10 (FIGS. 6D–6F), and 100 (FIGS. 6G–6I), and a filter length of 20. Numerical results corresponding to FIG. 6 are shown in FIG. 7. FIG. 6 includes the 'zero' plane, such that stability regions provided by the intersection of the Lyapunov difference with this plane can be visualized.

Note again, that A=0 corresponds to the LMS Wiener solution. At sufficiently high SNR, for all candidates, $V_{k+1}-V_k=0$ for A=B=0, i.e., operation at the Wiener solution with $Q_k=0$. A notable exception to this is candidate 3, for which $V_{k+1}-V_k>0$ for A=0 and B=0 and SNR=2, due to the breakdown of the approximation of the leakage factor in Eq. 43 for low SNR.

For A=0 and B>0, the Wiener solution is unstable, which is consistent with the bias of leaky LMS algorithms away from the Wiener solution. The uniform asymptotic stability region in FIG. 6 is the region for which $V_{k+1}-V_k<0$. At sufficiently high SNR, this stability region is largest for candidate 3, followed by candidate 1. Candidate 2 provides the smallest overall stability region.

For example, if one takes a slice of each FIG. 6 at B=−1, the resulting range of A for which $V_{k+1}-V_k>0$ is largest for candidate 2. However, the likelihood of obtaining such combinations of A and B in practice is remote for sufficiently high SNR and a stationary or slowly time varying Wiener solution. Near the origin, which is the most likely operating point, the stability region for all three candidates is similar for sufficiently high SNR.

Performance of each candidate tuning law is assessed by examining both the size of the stability region and the gradient of $V_{k+1}-V_k$ with respect to parameters A and B. Note from Eq. 32 that the gradient of $V_{k+1}-V_k$ approaches zero as $\lambda_k$ approaches one and $\mu_k$ approaches zero (i.e., stability, but no convergence). In the stable region of FIG. 6, the gradient of the Lyapunov difference is larger for tuning that provides an aggressive step size.

Thus, a tuning law providing a more negative $V_{k+1}-V_k$ in the stable region should provide the best performance, while the tuning law providing the largest region in which $V_{k+1}-V_k<0$ provides the best stability. FIG. 7 records the maximum and minimum values of $V_{k+1}-V_k$ for the range of A and B examined, showing candidate 2 should provide the best performance (and least stability), while candidate 3 provides the best overall stability/performance tradeoff for high SNR, followed by candidates 1 and 2.

For all three candidates, leakage factor approaches one as signal-to-noise ratio increases, as expected, and candidate 2 provides the most aggressive step size, which relates to the larger gradient of $V_{k+1}-V_k$ and thus the best predicted performance. An alternate view of $V_{k+1}-V_k$ as it relates to performance is to consider $V_{k+1}-V_k$ as the rate of change of energy of the system. The faster the energy decreases, the faster convergence, and hence the better performance.

The results of this stability analysis do not require a stationary Wiener solution, and thus these results can be applied to reduction of both stationary and nonstationary $X_k$. The actual value of the Wiener solution, which is embedded in the parameters A and B does affect the stability region, and it is possible, that any of the three candidates can be instantaneously unstable given an inappropriate combination of A and B.

Nevertheless, it is appropriate to use the graphical representation of FIG. 6 to determine how close to the Wiener solution one can operate as a measure of performance and to use the size of the stability region as a measure of stability. In cases where the Wiener solution is significantly time variant, the possibility of operating far from the Wiener solution increases, requiring more attention to developing candidate tuning laws that enhance the stability region for larger magnitudes of parameters A and B.

Experimental Results

The three candidate Lyapunov tuned leaky LMS algorithm are evaluated and compared to i) an empirically tuned, fixed leakage parameter leaky, normalized LMS algorithms (LNLMS), and ii) an empirically tuned normalized LMS algorithm with no leakage parameter (NLMS). The comparisons are made for a low-frequency single-source, single-point noise cancellation system in an acoustic test chamber (42, FIG. 3) designed to provide a highly controlled and repeatable acoustic environment with a flat frequency response over the range of 0 to 200 Hz for sound pressure levels up to 140 dB.

The system under study is a prototype communication headset earcup. The earcup contains an external microphone to measure the reference signal, an internal microphone to measure the error signal, and an internal noise cancellation speaker to generate $y_k$. Details regarding the prototype are given above in connection with FIG. 3.

The reference noise is from an F-16, a representative high-performance aircraft that exhibits highly nonstationary characteristics and substantial impulsive noise content. The noise source is band limited at 50 Hz to maintain a low level of low frequency distortion in the headset speaker and 200 Hz, the upper limit for a uniform sound field in the low frequency test cell.

FIG. 8 shows the low frequency regime of the reference noise power spectrum along with statistically determined upper and lower bounds on the power spectrum that indicate the degree of nonstationarity of the noise source. To obtain these bounds, the variation in the power spectral density (PSD) of a three-second-noise sample was calculated. The three-second sample was then divided into 100 equal length segments, and the PSD of each 0.03-second segment was determined. From these sampled spectrums, the minimum and maximum PSD as a function of frequency was determined, providing upper and lower bounds on the power spectrum.

The noise floor of the test chamber 42 is 50 dB. Without active noise cancellation, the earmuff provides approximately 5 dB of passive noise reduction over the 50 to 200 Hz frequency band. The amplitude of the reference noise source is established to evaluate algorithm performance over a 20 dB dynamic range, i.e., sound pressure levels of 80 dB and 100 dB, as measured inside the earcup after passive attenuation. The difference in sound pressure levels tests the ability of the tuned leaky LMS algorithms to adapt to different signal-to-noise ratios.

The two noise amplitudes represent signal-to-noise ratio (SNR) conditions for the reference microphone measurements of 35 dB and 55 dB, respectively. For the F-16 noise source and 100 dB SPL (55 dB SNR), analysis of $V_{k+1}-V_k$ of Eq. 32 for Lyapunov tuned candidates shows statistically determined bounds on B of $-0.6<B<0.6$, while for the 80 dB SPL (35 dB SNR), statistically determined bounds on B are $-3<B<3$. Thus, FIG. 6, which gives the $V_{k+1}-V_k$ surface for each candidate algorithm, shows that by lowering SNR to 35 dB, instability is possible for all three candidates, as the fixed step size is chosen for worst case conditions on B of $-1<B<1$.

Thus, in addition to eliciting stability and performance tradeoffs, the 80 dB SPL noise source tests the limits of stability for the three candidate algorithms. The quantization noise magnitude is 610e-6 V, based on a 16-bit round-off A/D converter with a ±10 V range and one sign bit. The candidate LMS algorithms are implemented experimentally using a dSPACE DS1103 DSP board. A filter length of 250 and weight update frequency of 5 kHz are used. The starting point for the noise segments used in the experiments is nearly identical for each test, so that noise samples between different tests overlap.

In the first part of this comparative study, the empirically tuned NLMS and LNLMS filters with constant leakage parameter and the traditional adaptive step size of Eq. 34 are tuned for the 100 dB SPL and subsequently applied without change to the system for the 80 dB SPL. On the other hand, the constant leakage parameter LNLMS filter is empirically tuned for 80 dB and subsequently applied to the 100 dB SPL test condition.

These two empirically tuned algorithms are denoted LNLMS(100) and LNLMS(80), respectively. For both filters, $\mu_o=1/3$, and the respective leakage parameter is given in FIG. 9. Application of the algorithm tuned for a specific SPL to cancellation of noise not matching the tuning conditions demonstrates the loss of performance that results under constant tuning parameters that would be required for a noise cancellation system subject to this 20 dB dynamic range. In all experiments, the weight vector elements are initialized as zero.

FIG. 10 shows experimental results for these three filters (NLMS, LNLMS(100), and LNLMS(80)) operating at 100 dB SPL. Of the empirically tuned filters, the NLMS algorithm and the LNLMS tuned for 100 dB algorithm show similar performance, while the LNLMS algorithm tuned for 80 dB shows significant performance reduction at steady-state. Here, SNR is sufficiently high that only a small amount of leakage is required to guarantee stability, thus performance degradation due to the leakage factor is minimal. Note that although the NLMS algorithm is stable after five seconds of operation, a slow weight drift occurs, such that the leakage factor is required.

FIG. 11 shows results for the 80 dB SPL. Here, the low SNR causes weight instability in the NLMS algorithm during the five second experiment. The mismatch in tuning conditions, i.e., using the LNLMS(100) algorithm under 80 dB SPL conditions also results in weight drift instability. Evidence of instability of the NLMS and LNLMS(100) algorithms at 80 dB is shown in time histories of the root-mean square (RMS) weight vector in FIGS. 12A and 12B. The results of FIGS. 10 through 12 demonstrate both the loss of stability when using an overly aggressive (large) fixed parameter leakage parameter and the loss of performance when a less aggressive (small) leakage parameter is required in order to retain stability over large changes in the dynamic range of the reference input signal.

The Lyapunov based tuning approach provides a candidate algorithm that retains stability and satisfactory performance in the presence of the nonstationary noise source over the 20 dB dynamic range, i.e., at both 80 and 100 dB SPL. FIG. 13 shows performance at 100 dB SPL, and FIG. 14 shows performance at 80 dB SPL.

At 100 dB SPL (FIG. 13), all three candidate algorithms retain stability, and at steady-state, noise reduction performance of all three candidate algorithms exceeds that of empirically tuned leaky LMS algorithms. In fact, performance closely approximates that of the NLMS algorithm, which represents the best possible performance for a stable system, as it includes no performance degradation due to a leakage bias.

At 80 dB SPL (FIG. 14), candidates 2 and 3 are unstable at 80 dB SPL, reflecting the fact that candidate algorithms do not necessarily guarantee uniform asymptotic stability when assumptions regarding bounds on measurement noise are exceeded. Candidate 3, which was predicted by Lyapunov analysis to provide the best stability characteristics of the three candidates retains stability and provides a steady-state SPL attenuation exceeding that of the LNLMS(80) by 5 dB.

Since the LNLMS(80) is the best performing stable fixed leakage parameter algorithm available, the performance improvement is significant. Note that comparison of performance at 80 dB SPL to the NLMS algorithm cannot be made, because the NLMS algorithm is unstable for the 80 dB SPL (35 dB SNR).

FIG. 15 shows the RMS weight vector histories for both 80 dB and 100 dB reference input sound pressure levels, providing experimental evidence of stability of all three candidates at 100 dB SPL and of candidate 3 at 80 dB SPL.

Performance gains of Lyapunov tuned candidates over the fixed leakage parameter LMS algorithms are confirmed by the mean and variance of the leakage factor for each candidate, as shown in FIG. 9. For all three candidates, the variance of the leakage factor is larger for the 80 dB test condition that for the 100 dB condition, as expected, since the measured reference signal at 80 dB represents lower average and instantaneous signal-to-noise ratios. Moreover, with the exception of candidate 1 at 80 dB, the mean leakage factor is larger than that provided by empirical tuning.

Hence, on average, the Lyapunov tuned LMS algorithms are more aggressively tuned and operate closer to the Wiener solution, providing better performance over a large dynamic range than constant leakage factor algorithms.

Finally, relative performance, which is predicted to be most aggressive for candidate 2, followed by candidates 3 and 1, respectively, is seen in FIG. 14. Candidate 2 provides the fastest convergence and the largest SPL attenuation of the three candidates.

The experimental results provide evidence that the method of tuning an adaptive Leaky LMS Filter according to the algorithm of the present invention provides stability and performance gains which result in the reduction of highly nonstationary noise for an optimized combination of both adaptive step size and adaptive leakage factor without requiring empirical tuning, with candidate 3 providing the best overall stability and performance tradeoffs.

In accordance with another aspect of the present invention, hybridization of a traditional feedback control law with a feedforward control law improves ANR performance and stability margins. The Lyapunov-tuned feedforward controller described herein has excellent response in systems with time-varying signal-to-noise ratio. Acting alone, the algorithm(s) disclosed above substantially improves ANR performance over traditional LMS filters and exhibits excellent performance for non-stationary noise sources, and good performance for non-stationary noise sources.

FIG. 17 shows a hybrid feedforward-feedback ANR topology in accordance with the present invention. A reference microphone 100 measures the primary source, which enters the unknown acoustic process H(z) 102, and the error signal 104 remaining after ANR is measured by a microphone 106. In the feedforward component, an adaptive LMS filter, provides a cancellations signal $-y_k$, 108. Here, the feedforward system can be thought of as providing a smaller error signal for the feedback controller to act on, since it models the unknown acoustic process, and thus the system can tolerate an overall increase in the feedback or feedforward controller gain without destabilizing the system. Alternatively, one can consider a feedback controlled system as being acted upon by the feedforward controller, which because it is adaptive, performs its task whether or not the feedback control component is in place.

In experimental evaluation of the architecture, a broadband, feedback controller providing 5–10 dB of attenuation in the 40 Hz to 1600 Hz frequency band is paired with the feedforward controller, which is tuned according to one aspect of the present invention. Both the feedback and feedforward components are implemented digitally. Because of this, no additional hardware components are required to add the feedback component beyond those used for the feedforward controller. FIG. 18 shows sample experimental results. At low frequencies (<100 Hz), the feedback component provides 7–8 dB of active attenuation, and the feedforward component, which is tuned according to method disclosed herein provides 15–27 dB of attenuation. However, the hybrid system demonstrates overall performance that is greater than the sum of the individual components at frequencies below 80 Hz. The exceptional performance of the hybrid system is achieved by pairing the feedforward controller tuned in accordance with the method disclosed herein with the traditional infinite impulse response feedback controller.

It is known that feedback controllers exhibit less sensitivity than feedforward controllers to noise source characteristics. Thus, for non-stationary noise sources, the hybrid system exhibits the positive characteristics of the Lyapunov-tuned feedforward system combined with the positive characteristics of a feedback controller in exhibiting less sensitivity to noise source characteristics.

FIG. 19 shows measured stability margins of a hybrid controller from experimental evaluation of the system when applied to ANR in a hearing protector. Measurements were made using the low frequency acoustic test cell and digital signal processing development system described herein. Stability margin is measured by the tolerable increase in the feedforward controller gain ($K_{ff}$) before the system shows evidence of instability with and without the feedback component in place. With the hybrid system, gain margin improves by a factor of 2 to over 1000 through the band evaluated.

It is important to note that the present invention is not intended to be limited to a device or method which must satisfy one or more of any stated or implied objects or features of the invention. It is also important to note that the present invention is not limited to the preferred, exemplary, or primary embodiment(s) described herein. Modifications and substitutions by one of ordinary skill in the art are considered to be within the scope of the present invention, which is not to be limited except by the following claims.

What is claimed is:

1. A method of tuning an adaptive feedforward noise cancellation algorithm, comprising the acts of:

providing a feedback active noise reduction (ANR) circuit, for providing an ANR error signal;

providing a feedforward LMS tuning algorithm including at least first and second time varying parameters wherein said feedforward LMS tuning algorithm includes the formulas:

$$y_k = W_k^T X_k \text{ and}$$

$$W_{k+1} = \lambda_k W_k + \mu_k X_k e_k$$

adjusting said at least first and second time varying parameters as a function of instantaneous measured acoustic noise, a weight vector length and measurement noise variance, wherein said time varying parameters include:

$$\mu_k = \frac{\mu_o \lambda_k}{(X_k + Q_k)^T (X_k + Q_k)}$$

$$\lambda_k = \frac{(X_k + Q_k)^T (X_k + Q_k) - 2L\sigma_q^2}{(X_k + Q_k)^T (X_k + Q_k)}$$

wherein $X_k = X_k + Q_k$ is a measured reference signal; $Q_k$ is measurement noise, including electronic noise and quantization noise;

$\sigma_q^2$ is the known or measured variance of the measurement noise;

L is the length of the LMS weight vector $W_k$; and $e_k$ is an error signal which is the net result of both the feedforward method and the feedback circuit.

2. The method of claim 1 wherein the output of the filter $y_k$ is multiplied by a feedforward proportionality constant $K_{ff}$ to produce a feedforward acoustic noise cancellation signal $K_{ff} y_k$ and wherein the error signal $e_k$ is acted on by a digital infinite impulse response filter so as to produce a cancellation signal $r_k$, which is multiplied by a feedback proportionality constant $K_{fb}$ and the sum of the feedforward and feedback components $K_{ff} y_k + K_{fb} r_k$ provides a total noise cancellation signal.

3. The method of claim 2 wherein said ANR error signal of feedback active noise reduction (ANR) circuit and said feedforward LMS tuning algorithm each provide an active noise reduction performance value that is greater than a sum of said ANR circuit and said LMS tuning algorithm.

4. A method of tuning an algorithm for providing noise cancellation, comprising the acts of:

receiving a measured reference signal, the measured reference signal including a measurement noise component having a measurement noise value of known variance; and generating an acoustic noise cancellation signal according to the formulas:

$$y_k = W_k^T X_k$$

$$W_{k+1} = \lambda_k W_k + \mu_k X_k e_k$$

wherein time varying parameters $\lambda_k$ and $\mu_k$ are determined according to the formulas:

$$\mu_k = \frac{\mu_o \lambda_k}{(X_k + Q_k)^T (X_k + Q_k)}$$

-continued $$\lambda_k = \frac{(X_k + Q_k)^T (X_k + Q_k) - 2L\sigma_q^2}{(X_k + Q_k)^T (X_k + Q_k)}$$

wherein $X_k = X_k + Q_k$ is a measured reference signal;

$Q_k$ is electronic noise and quantization;

$\sigma_q^2$ is a known variance of the measurement noise;

L is the length of weight vector $W_k$; and $e_k$ is an error signal which is the net result of both a feedforward tuning method and a feedback active noise reduction method.

5. A method of tuning a least mean square (LMS) filter comprising the acts of:

providing a feedback active noise reduction (ANR) circuit, for providing an ANR error signal;

formulating a Lyapunov function of a LMS filter weight vector, a reference input signal, a measurement noise on the measured reference input signal, a time varying leakage parameter $\lambda_k$, and a step size parameter $\mu_k$;

using the resultant Lyapunov function to identify formulas for computing the time varying leakage parameter $\lambda_k$ and step size parameter $\mu_k$ that maximize stability and performance of the resultant LMS filter weight vector update equation $$W_{k+1} = \lambda_k W_k + \mu_k e_k X_k$$

wherein said time varying parameters determined are $$\mu_k = \frac{\mu_o \lambda_k}{(X_k + Q_k)^T (X_k + Q_k)}$$

$$\lambda_k = \frac{(X_k + Q_k)^T (X_k + Q_k) - 2L\sigma_q^2}{(X_k + Q_k)^T (X_k + Q_k)}$$

wherein $X_k = X_k + Q_k$ is a measured reference signal;

$Q_k$ is electronic noise and quantization;

$\sigma_q^2$ is a known variance of the measurement noise;

L is the length of weight vector $W_k$; and $e_k$ is an error signal which is the net result of both the ANR circuit and the LMS filter.

6. A method of tuning an adaptive feedforward noise cancellation algorithm, comprising the acts of:

providing a feedback active noise reduction (ANR) circuit, for providing an ANR error signal;

providing a feedforward LMS tuning algorithm including at least first and second time varying parameters wherein said feedforward LMS tuning algorithm includes the formulas:

$$y_k = W_k^T X_k; \text{ and}$$

$$W_{k+1} = \lambda_k W_k + \mu_k X_k e_k$$

adjusting said at least first and second time varying parameters as a function of instantaneous measured acoustic noise, a weight vector length and measurement noise variance, wherein said time varying parameters include:

$$\mu_k = \frac{\mu_o \lambda_k}{(X_k + Q_k)^T (X_k + Q_k)}$$

$$\lambda_k = \frac{(X_k + Q_k)^T (X_k + Q_k) - 2L\sigma_q^2}{(X_k + Q_k)^T (X_k + Q_k)}$$

wherein $X_k = X_k + Q_k$ is a measured reference signal; $Q_k$ is measurement noise, including electronic noise and quantization noise; $\sigma_q^2$ is the known or measured variance of the measurement noise; L is the length of the LMS weight vector $W_k$; and $e_k$ is an error signal which is the net result of both the feedforward method and the feedback circuit, and further wherein the output of the filter $y_k$ is multiplied by a feedforward proportionality constant $K_{ff}$ to produce a feedforward acoustic noise cancellation signal $K_{ff} y_k$ and the error signal $e_k$ is acted on by a digital infinite impulse response filter so as to produce a cancellation signal $r_k$, which is multiplied by a feedback proportionality constant $K_{fb}$ and the sum of the feedforward and feedback components $K_{ff} y_k + K_{fb} r_k$ provides a total noise cancellation signal.

7. The method of claim 6 wherein said ANR error signal of feedback active noise reduction (ANR) circuit and said feedforward LMS tuning algorithm each provide an active noise reduction performance value that is greater than a sum of said ANR circuit and said LMS tuning algorithm.

* * * * *